US012246096B2

(12) United States Patent
Baxter et al.

(10) Patent No.: US 12,246,096 B2
(45) Date of Patent: Mar. 11, 2025

(54) SELF-ASSEMBLED MICROCAPSULES WITH STIMULI-RESPONSIVE ORGANIC LIGANDS

(71) Applicant: The Regents of the University of California, Oakland, CA (US)

(72) Inventors: Ryan Baxter, Merced, CA (US); Sayantani Ghosh, Merced, CA (US)

(73) Assignee: The Regents of the University of California, Oakland, CA (US)

( * ) Notice: Subject to any disclaimer, the term of this patent is extended or adjusted under 35 U.S.C. 154(b) by 441 days.

(21) Appl. No.: 17/296,187

(22) PCT Filed: Nov. 20, 2019

(86) PCT No.: PCT/US2019/062460
§ 371 (c)(1),
(2) Date: May 21, 2021

(87) PCT Pub. No.: WO2020/106875
PCT Pub. Date: May 28, 2020

(65) Prior Publication Data
US 2022/0008347 A1 Jan. 13, 2022

Related U.S. Application Data

(60) Provisional application No. 62/770,473, filed on Nov. 21, 2018.

(51) Int. Cl.
*A61K 9/00* (2006.01)
*A61K 9/14* (2006.01)
*A61K 9/50* (2006.01)

(52) U.S. Cl.
CPC .......... *A61K 9/5089* (2013.01); *A61K 9/0009* (2013.01); *A61K 9/143* (2013.01); *A61K 9/5015* (2013.01)

(58) Field of Classification Search
None
See application file for complete search history.

(56) References Cited

U.S. PATENT DOCUMENTS

| 2011/0177005 A1 | 7/2011 | Rapoport et al. |
| 2016/0000918 A1* | 1/2016 | Cheon .................... A61K 9/513 600/12 |
| 2018/0250237 A1 | 9/2018 | Lin et al. |
| 2020/0230066 A1* | 7/2020 | Quint .................. A61K 9/0004 |

FOREIGN PATENT DOCUMENTS

| WO | WO 2017/015145 | 1/2017 |
| WO | WO 2019/071258 | 4/2019 |

OTHER PUBLICATIONS

Socratic (https://socratic.org/questions/how-does-voltage-affect-a-magnetic-field (2014)) (Year: 2014).*
Rodarte et al (Self-assembled nanoparticle micro-shells templated by liquid crystal sorting. Soft Matter, 2015, 11, 1701) (Year: 2015).*
Wojtechi et al (Optimizing the formation of 2,6-bis(N-alkylbenzimidazolyl)pyridine-containing [3]catenates through component design. Chem. Sci., 2013, 4, 4440) (Year: 2013).*
Buongiorno et al (Structure and function of atypically coordinated enzymatic mononuclear non-heme-Fe(II) centers. Coordination Chemistry Reviews 257 (2013) 541-563). (Year: 2013).*
McKenzie et al (Metallo-Responsive Liquid Crystalline Monomers and Polymers. Chem. Mater. 2011, 23, 3525-3533), (Year: 2011).*
Damavandi et al (Bis(imino)pyridine-Iron(II) Complexes for Ethylene Polymerization. Polymer Science, Series B, 2017, vol. 59, No. 1, pp. 1-6). (Year: 2017).*

* cited by examiner

*Primary Examiner* — Jake M Vu
(74) *Attorney, Agent, or Firm* — Rudy J. Ng; Melissa Nakamoto; Bozicevic, Field & Francis LLP

(57) ABSTRACT

Self-assembled organic ligand functionalized microcapsules encapsulating one or more substrates, which release the substrates upon activation with a power source, are provided. Compositions that include these microcapsules, as well as methods of making the microcapsules and releasing the encapsulated substrates are also provided. The structures, compositions and methods find use in a variety of applications, such as drug and cell encapsulation technologies, for direct delivery, control, and activation of medicines and therapies to specific tissues in a living host.

18 Claims, 6 Drawing Sheets

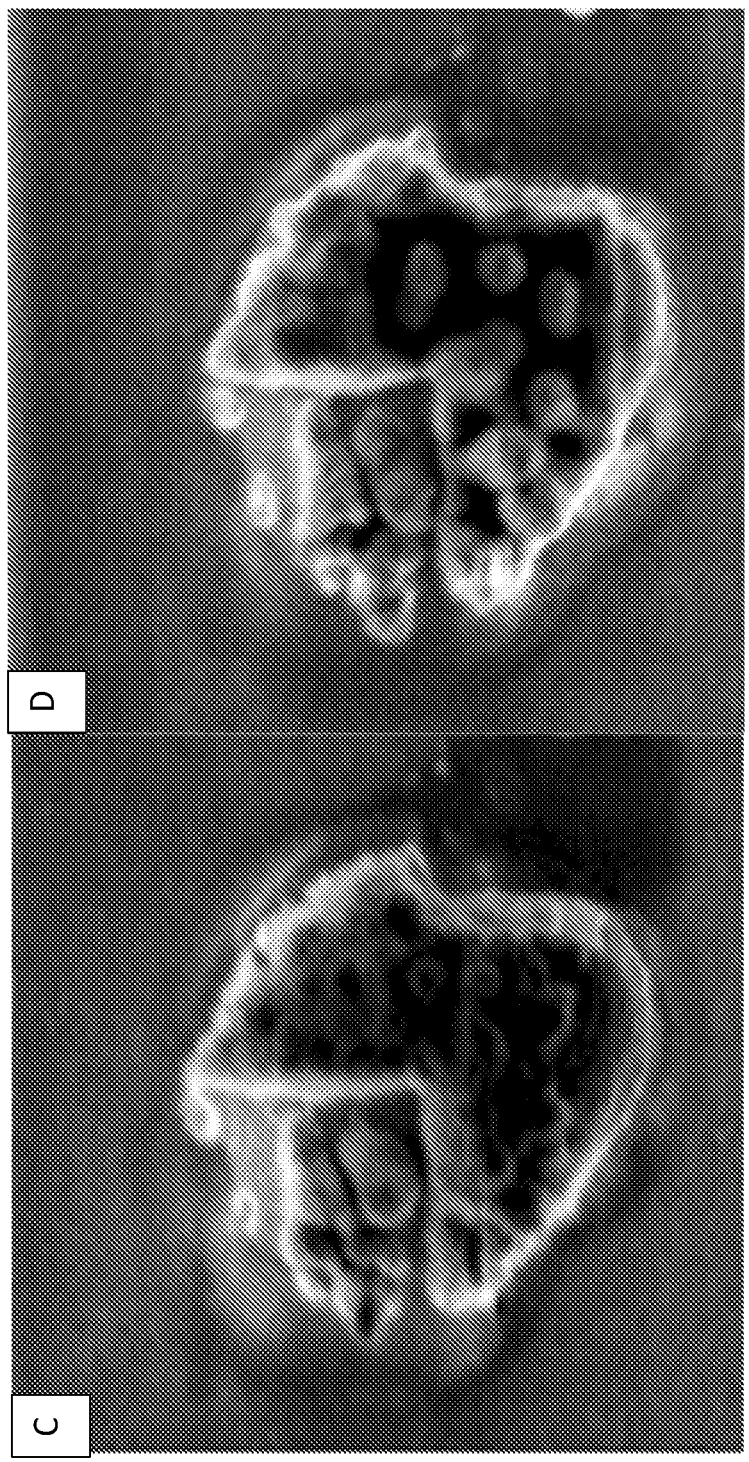
FIG. 5, continued

SELF-ASSEMBLED MICROCAPSULES WITH STIMULI-RESPONSIVE ORGANIC LIGANDS

CROSS-REFERENCE TO RELATED APPLICATIONS

This application claims benefit to U.S. Provisional Application No. 62/770,473, filed Nov. 21, 2018, the disclosure of which is incorporated herein by reference.

STATEMENT REGARDING FEDERALLY SPONSORED RESEARCH

This invention was made with government support under Grant Number HRD-1547848 awarded by the National Science Foundation. The government has certain rights in the invention.

INTRODUCTION

Robust structures for encapsulating cargo, configured for rapid controlled discharge of its cargo at a particular time and location pose a significant design challenge. Particularly challenging, is the design of structures configured for targeted delivery of its cargo to an individual without disruption to the surrounding living tissue of that individual. Previous efforts in this area have focused on polymer-based microcapsules sensitive to thermal gradients, pH, laser and light. With advances in nanotechnology, incorporating nanomaterials of varied compositions and morphologies in polymer or gel-based matrices has led to the development of structures configured to remotely control the release process using stimuli such as electric and magnetic fields, as well as optical excitation. However, existing microcapsule cargo delivery systems are not suitable for controlled release applications in a living host since high power and temperatures are needed in order to release the encapsulated cargo, resulting in damage to the surrounding healthy tissue in the living host.

SUMMARY

Self-assembled microcapsules, functionalized with organic ligands which undergo electron transfer upon activation with one or more external stimulus, are provided. Compositions and kits that include these microcapsules, as well as methods of delivering one or more substrates encapsulated inside the microcapsules to an individual, are also provided. The structures, compositions and methods find use in a variety of applications, such as drug and cell encapsulation technologies, for direct delivery, control, and activation of medicines and therapies to specific tissues in a living host.

Aspects of the present disclosure include a self-assembled microcapsule composed of nanoparticles and stimuli-responsive organic ligands attached to the nanoparticles, wherein the organic ligands undergo electron transfer upon activation with one or more external stimulus to produce a nanomaterial with openings.

In some embodiments of the present disclosure, the organic ligand is attached to the nanoparticles through more than one binding site.

In some embodiments, the organic ligands are electro-responsive and the external stimulus to produce the nanomaterial with openings is an electrical input. In some embodiments, the electrical input is adjusted based on defined electronic properties of the organic ligand. In some embodiments, the electrical input is applied at a voltage of from 300 mV to 3 kV. In certain embodiments, the electrical input is applied at a voltage of from 300 mV to 1500 mV.

In some embodiments, the organic ligands are sound-responsive and the external stimulus to produce the nanomaterial with openings is sound energy. In some embodiments, the sound energy is applied at a frequency of from 20 kHz to 40 kHz. In certain embodiments, the sound energy is applied at a frequency of from 25 kHz to 35 kHz.

In some embodiments, the electrical input is applied for a duration of one hour or less to produce the nanomaterial with openings.

In some embodiments, the sound energy is applied for a duration of one hour or less to produce the nanomaterial with openings.

In some embodiments of the present disclosure, the self-assembled microcapsule includes an organic ligand of formula (I):

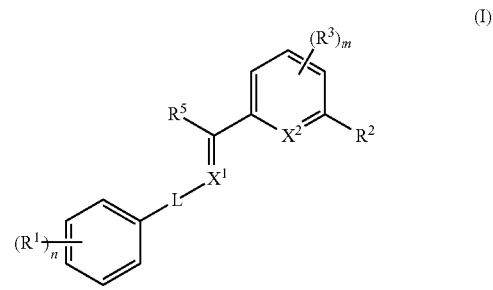

wherein
$X^1$ and $X^2$ are each independently selected from N and $CR^7$, wherein each $R^7$ is independently selected from H, halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
L is a bond or a linker;
$R^1$ and $R^3$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
$R^2$ is selected from H, halogen, hydroxyl, azido, acyl, substituted acyl, imine, substituted imine, alkyl, substituted alkyl, alkenyl, substituted alkenyl, alkynyl, substituted alkynyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof $R^5$ is selected from H, alkyl, substituted alkyl, aryl, and substituted aryl;

n is an integer from 0 to 5; and m is an integer from 0 to 3.

In some embodiments of the present disclosure, the self-assembled microcapsule includes an organic ligand of formula (IA):

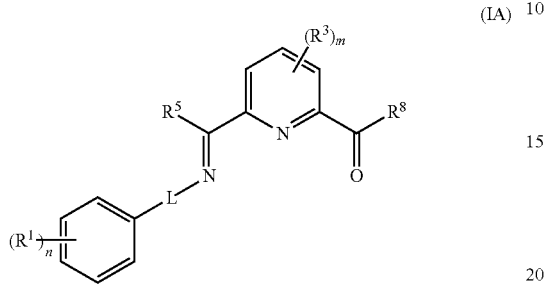

wherein:

L is a bond, or a linker;

$R^1$ and $R^3$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

$R^5$ and $R^8$ are each independently selected from H, alkyl, substituted alkyl, aryl, and substituted aryl;

n is an integer from 0 to 5; and m is an integer from 0 to 3.

In some embodiments of formulae (I) or (IA), n is 2 and each $R^1$ is an alkyl group. In certain embodiments of formula (IA), $R^5$ and $R^8$ are both alkyl groups.

In some embodiments of the present disclosure, the self-assembled microcapsule includes an organic ligand of formula (II):

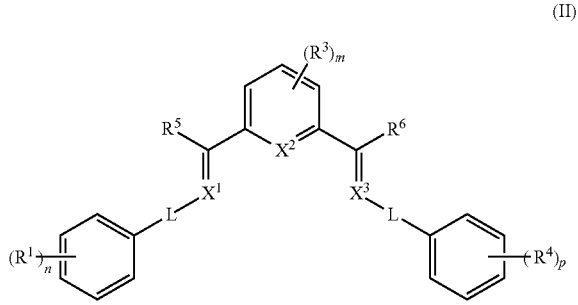

wherein $X^1$, $X^2$ and $X^3$ are each independently selected from N and $CR^7$, wherein each $R^7$ is independently selected from H, halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

L is a bond, or a linker;

$R^1$, $R^3$ and $R^4$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

$R^5$ and $R^6$ are each independently selected from H, alkyl, substituted alkyl, aryl, and substituted aryl;

n is an integer from 0 to 5;

m is an integer from 0 to 3; and p is an integer from 0 to 5.

In some embodiments of the present disclosure, the self-assembled microcapsule includes an organic ligand of formula (IIA):

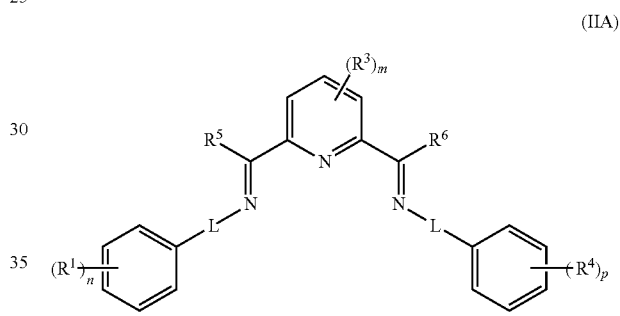

wherein:

L is a bond, or a linker;

$R^1$, $R^3$ and $R^4$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

$R^5$ and $R^6$ are each independently selected from H, alkyl, substituted alkyl, aryl, and substituted aryl;

n is an integer from 0 to 5;

m is an integer from 0 to 3; and p is an integer from 0 to 5.

In some embodiments of formulae (II) or (IIA), one or more of $R^1$, $R^3$ and $R^4$ is selected from $C_1$-$C_8$ alkoxy substituted with an amine, a thiol or hydroxyl group, and $C_1$-$C_8$ alkyl substituted with an amine, thiol or hydroxyl group. In certain embodiments of formula (II) or (IIA), $R^1$, $R^3$ and $R^4$ is selected from —O(CH$_2$)$_q$NH$_2$, —O(CH$_2$)$_q$SH, —O(CH$_2$)$_q$OH, —(CH$_2$)$_q$NH$_2$, —(CH$_2$)$_q$SH and —(CH$_2$)$_q$OH, wherein each q is independently an integer from 1 to 8.

In some embodiments of formula (II) or (IIA), $R^5$ and $R^6$ are both alkyl groups. In some embodiments, n and p are each 2 and $R^1$ and $R^4$ are each alkyl groups. In certain embodiments, the $R^1$ and $R^4$ alkyl groups are selected from methyl, ethyl, propyl, isopropyl, butyl, sec-butyl, tert-butyl, pentyl and hexyl. In some embodiments, each of the $R^1$ and $R^4$ alkyl groups are isopropyl.

In some embodiments of formula (II) or (IIA), n and p are each 1 and $R^1$ and $R^4$ are each alkoxy groups. In certain embodiments, each of the alkoxy groups are methoxy groups.

In some embodiments of the present disclosure, the self-assembled microcapsule includes an organic ligand selected from:

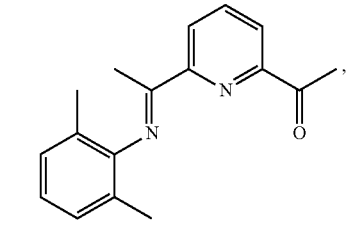
(1)

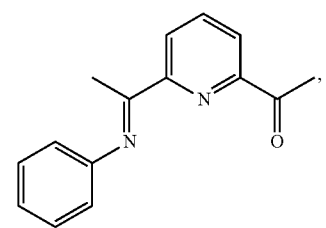
(2)

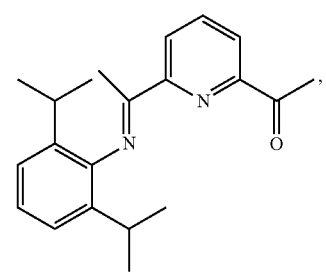
(3)

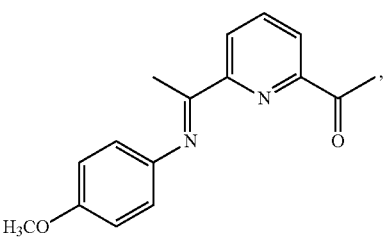
(4)

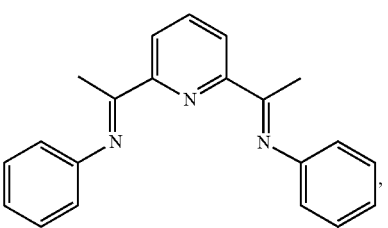
(5)

-continued

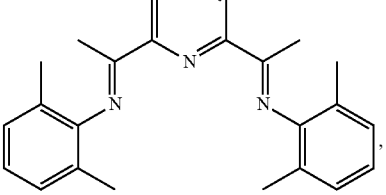
(6)

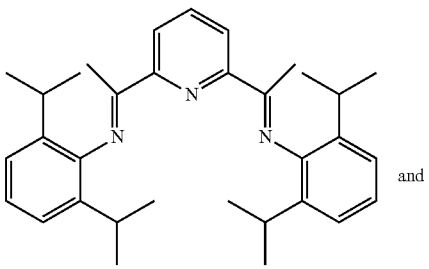
(7)
and

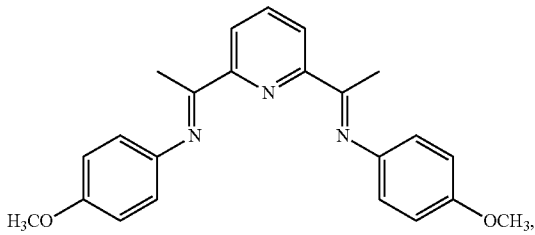
(8)

and combinations thereof.

In some embodiments of the self-assembled microcapsules, the mean inter-particle separation of the nanoparticles is from 1 nm to 100 nm. In some embodiments of the self-assembled microcapsules, the nanoparticles are composed of upconversion nanoparticles, plasmonic nanoparticles, or combinations thereof.

In some embodiments of the self-assembled microcapsules, the nanoparticles are composed of a material selected from a semiconductor material, a metal, a metal oxide, a metalloid, a metal coated material, an oxide, a magnetic material, a nanosome, a lipidsome and a polymer, and combinations thereof. In certain embodiments, the nanoparticles are composed of a material selected from gold nanoparticles, silver nanoparticles, zinc oxide nanoparticles, cadmium nanoparticles, tin nanoparticles, selenium nanoparticles, iridium nanoparticles, gold coated nanoparticles, silver coated nanoparticles and zinc coated nanoparticles, and combinations thereof. In certain embodiments the nanoparticles are composed of a material selected from iron oxide nanoparticles, cobalt nanoparticles, graphene coated iron oxide nanoparticles, graphene coated cobalt nanoparticles, silica coated iron oxide nanoparticles and silica coated cobalt nanoparticles, and combinations thereof. In some cases, the nanoparticles are composed of gold nanoparticles. In certain other cases, the nanoparticles are composed of non-metallic nanoparticles.

In some embodiments of the present disclosure, the self-assembled microcapsule has a spherical surface. In certain embodiments, the microcapsule has an average diameter of 200 nm to 2 µm. In certain embodiments of the self-assembled microcapsule, the nanoparticles have an average diameter of 1 nm to 100 nm.

In some embodiments of the present disclosure, the self-assembled microcapsule has a thickness of from 1% to 50% of the volume of the microcapsule.

In some embodiments of the present disclosure, one or more substrates is encapsulated inside the self-assembled microcapsule. In certain embodiments, at least one substrate is an active agent. In certain embodiments, at least one substrate is live cells. In certain embodiments, the substrate is release upon activation with the external stimulus. In certain cases, full release of the substrate is obtained in 5 minutes or less from the time of activation with the external stimulus.

Other aspects of the present disclosure include a composition including a liquid and a subject self-assembled microcapsule (e.g., as described herein) in the liquid. In some embodiments, the liquid is a pharmaceutically acceptable liquid or a mesomorphic material.

Further aspects of the present disclosure include a method of delivering one or more substrates to an individual. The method includes administering an effective amount of a self-assembled microcapsule composed of nanoparticles, stimuli-responsive organic ligands attached to said nanoparticles, and one or more substrates encapsulated inside the microcapsule; and applying one or more external stimulus, wherein the organic ligands undergo electron transfer upon activation with the external stimulus to rupture the microcapsule and release the one or more substrates. In some embodiments, the organic ligand has a structure of formula (I). In some embodiments, the organic ligand has a structure of formula (II). In some embodiments, the organic ligand is selected from compounds (1)-(8), or combinations thereof.

In some embodiments of the method of delivering one or more substrates to an individual, the self-assembled microcapsules are stable upon application of heat up to a temperature of from 100 to 240° C.

In some embodiments of the method of delivering one or more substrates to an individual, the organic ligands are electro-responsive and the external stimulus to rupture the microcapsule is an electrical input. In some embodiments, the electrical input is adjusted based on defined electronic properties of the organic ligand. In some embodiments, the electrical input is applied at a voltage of from 300 mV to 3 kV. In certain embodiments, the electrical input is applied at a voltage of from 300 mV to 1500 mV.

In some embodiments of the method of delivering one or more substrates to an individual, the organic ligands are sound-responsive and upon activation with sound energy the microcapsule ruptures. In some embodiments, the sound energy is applied at a frequency of from 20 kHz to 40 kHz. In certain embodiments, the sound energy is applied at a frequency of from 25 kHz to 35 kHz.

In some embodiments of the method of delivering one or more substrates to an individual, a mixture of self-assembled microcapsules, each comprising different stimuli-responsive organic ligands is administered. In some embodiments, the external stimulus is adjusted to selectively target a specific self-assembled microcapsule comprising an associated stimuli-responsive organic ligand within the mixture of self-assembled microcapsules.

In some embodiments of the method of delivering one or more substrates to an individual, the electrical input is applied for a duration of one hour or less to rupture the microcapsule. In some embodiments of the method of delivering one or more substrates to an individual, the sound energy is applied for a duration of one hour or less to rupture the microcapsule. In some embodiments of the method of delivering one or more substrates to an individual, full release of the substrate is obtained in 5 minutes or less from the time of application of the external stimulus.

In some embodiments of the method of delivering one or more substrates to an individual, one or more substrate is an active agent. In some embodiments, one or more substrate is live cells.

Other aspects of the present disclosure include a kit for delivering one or more substrates to an individual, including one or more containers comprising a subject self-assembled microcapsule (e.g., as described herein), and one or more substrates encapsulated inside the microcapsule.

TERMS

Figure 1:
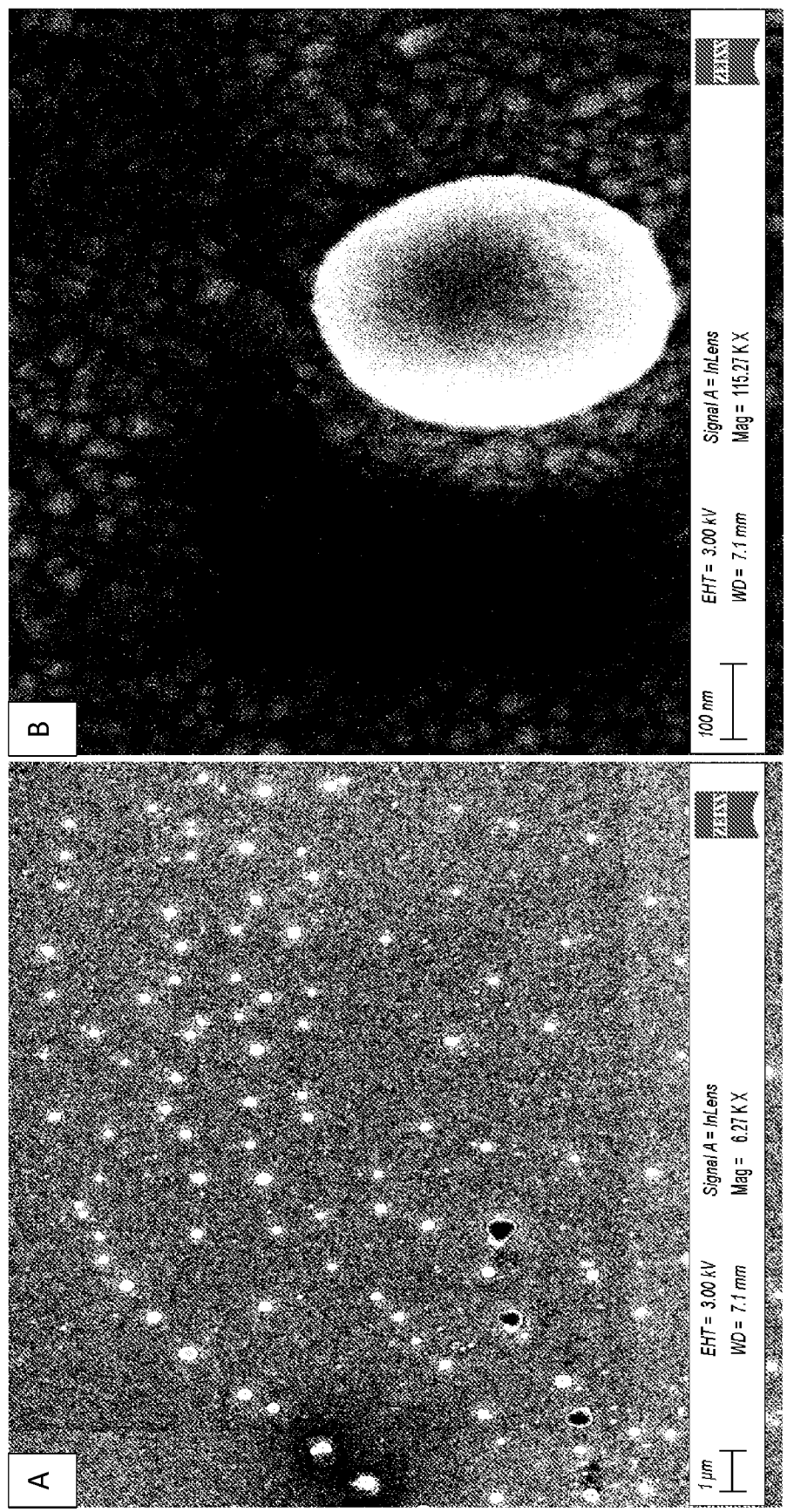
FIG. 1, panels A-B, show scanning electron microscope (SEM) images of self-assembled microcapsules composed of Cd/Sn/Se nanoparticles and exemplary compound (7). Panel A, shows a scanning electron microscope image of multiple self-assembled microcapsules composed of Cd/Sn/Se nanoparticles and exemplary compound (7). Panel B, shows a scanning electron microscope image of an intact self-assembled microcapsules composed of Cd/Sn/Se nanoparticles and exemplary compound (7).

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain (except for the $C_1$ carbon) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Thiol" refers to the group —SH.

The term "substituted thiol" refers to the group —SR where each R is independently selected from the group consisting of alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

By "linking" or "linker" as in "linking group," "linker moiety," etc., is meant a linking moiety that connects two groups via covalent bonds. The linker may be linear, branched, cyclic or a single atom. Examples of such linking groups include alkyl, alkenylene, alkynylene, arylene, alkarylene, aralkylene, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH$_2$)n-O—), epoxyimino (—O—NH—), epimino (—NH—), carbonyl (—CO—), etc. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol) unit(s) (e.g., —(CH$_2$—CH$_2$—O)—); ethers, thioethers, amines, alkyls (e.g., (C$_1$-C$_{12}$) alkyl), which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. Any convenient orientation and/or connections of the linkers to the linked groups may be used.

Unless indicated otherwise, the nomenclature of substituents that are not explicitly defined herein are arrived at by naming the terminal portion of the functionality followed by the adjacent functionality toward the point of attachment. For example, the substituent "aminoalkoxy" refers to the group NH$_2$-(alkyl)—O—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

As used herein, the term "active agent" is meant to refer to compounds that are therapeutic agents. The term also refers to chemical and therapeutic agents including live materials.

The term "live cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The term "mesomorphic material" refers to a material existing in a state of matter between liquid and crystal, such as a material that forms a mesomorphic state or mesophase. In some cases, the mesomorphic material is a liquid crystalline liquid or liquid crystal (LC). In some cases, the mesomorphic state or mesophase is a state or phase intermediate between that of the anisotropic crystal and that of the isotropic liquid. There are several mesomorphic states or forms, such as but not limited to, the semectic mesophase and the cholesterolic or nematic mesophase. In some cases the mesomorphic material is thermotropic.

DETAILED DESCRIPTION

Self-assembled stimuli-responsive organic ligand functionalized microcapsules, which undergo electron transfer upon activation with one or more external stimulus to provide a nanomaterial with openings, are disclosed herein. Compositions that include these microcapsules, as well as methods of releasing an encapsulated substrate from the microcapsules are also provided. The structures, compositions and methods find use in a variety of applications, such as drug and cell encapsulation technologies, for direct delivery, control, and activation of medicines and therapies to specific tissues in an individual.

Self-Assembled Microcapsules

Aspects of the present disclosure include self-assembled microcapsules composed of nanoparticles and stimuli-responsive organic ligand attached to the said nanoparticles. By "nanoparticles" is meant particles that have a size range in the nanometer (nm) scale. For example, a nanoparticle may have a size (e.g., largest dimension) of 1000 nm or less, such as a size ranging from 0.1 nm to 1000 nm. Self-assembled microcapsules of the present disclosure include structures having a shape that extends in three dimensions, such as length, width and height. Three-dimensional structures are distinct from one-dimensional structures (e.g., linear structures) and two-dimensional structures (e.g., planar structures).

The self-assembled microcapsules of the present disclosure include structures having a shell configuration. The term "shell" or "shell configuration" as used herein describes structures where a surface at least partially, and sometimes completely, encloses a space or material. A shell or shell configuration may also be referred to as a "capsule" or "microcapsule". A shell may partially or completely enclose the space or material. For instance, a shell may partially enclose the space or material, such as enclose 50% or more of the space or material, or 60% or more, or 70% or more, or 80% or more, or 90% or more, or 95% or more, or 97% or more, or 99% or more of the space or material. Partial enclosure of a space or material includes embodiments where the surface is substantially contiguous and has one or more voids (e.g., holes) in the surface, and also includes embodiments where the surface is substantially continuous, but the surface does not extend to completely enclose the space or material. In other embodiments, the shell completely encloses the space or material, such that the surface is substantially continuous without significant discontinuities (e.g., voids or holes) in the surface.

Surfaces with a shell configuration may have various shapes and sizes. For instance, shell configurations include, but are not limited to, regular shapes such as spherical shells, ellipsoid shells, cylinder shells, cone shells, cube shells, cuboid shells, pyramidal shells, torus shells, and the like. In other embodiments, the shell may have an irregular shape. In certain embodiments, structures of the present disclosure have a shell configuration, where the shell configuration is a spherical surface (i.e., a spherical shell). By "microcapsule" or "microcapsule configuration" is meant the structure has a size range in the micrometer (μm) scale. For example, a microstructure may have a size (e.g., largest dimension) of 100 μm or less, such as a size ranging from 100 nm to 100 μm (0.1 μm to 100 μm), 1 nm to 100 nm (0.001 μm to 0.1 μm).

In certain embodiments, the structures are microcapsules as described above, where the microcapsule have a size of 1000 μm or less, such as 950 μm or less, or 900 μm or less, or 850 μm or less, or 800 μm or less, or 750 μm or less, or 700 μm or less, or 650 μm or less, or 600 μm or less, or 550 μm or less, or 500 μm or less, or 450 μm or less, or 400 μm or less, or 350 μm or less, or 300 μm or less, or 250 μm or less, or 200 μm or less, or 150 μm or less, or 100 μm or less, or 90 μm or less, or 80 μm or less, or 70 μm or less, or 60 μm or less, or 50 μm or less, or 40 μm or less, or 30 μm or less, or 20 μm or less, or 10 μm or less, or 9 μm or less, or 8 μm or less, or 7 μm or less, or 6 μm or less, or 5 μm or less, or 4 μm or less, or 3 μm or less, or 2 μm or less, or 1 μm or less, or 0.75 μm or less, or 0.5 μm or less, or 0.25 μm or less, or 0.1 μm or less, or 0.075 μm or less, or 0.05 μm or less, or 0.025 μm or less, or 0.01 μm or less. In some instances, the microcapsules have a size ranging from 0.01 μm to 1000 μm, 0.025 μm to 1000 μm, 0.05 μm to 1000 μm, 0.075 μm to 1000 μm, 0.1 μm to 1000 μm, such as from 0.25 μm to 1000 μm, or 0.5 μm to 1000 μm, or 0.5 μm to 900 μm, or 0.5 μm to 800 μm, or 0.5 μm to 700, or 0.5 μm to 600 μm, or 0.5 μm to 500 μm, or 0.5 μm to 400 μm, or 0.5 μm to 300 μm, or 0.5 μm to 250 μm, or 0.5 μm to 200 μm, or 0.5 μm to 150 μm, or 0.5 μm to 100 μm, or 0.5 μm to 90 μm, or 0.5 μm to 80 μm, or 0.5 μm to 70 μm, or 0.5 μm to 60 μm, or 0.5 μm to 50 μm, or 0.5 μm to 40 μm, or 0.5 μm to 30 μm, or 0.5 μm to 20 μm, or 0.5 μm to 10 μm, or 0.5 μm to 9 μm, or 0.5 μm to 8 μm, or 0.5 μm to 7 μm, or 0.5 μm to 6 μm, or 0.5 μm to 5 μm, or 0.5 μm to 4 μm, or 0.5 μm to 3 μm, or 0.5 μm to 2 μm, or 0.5 μm to 1 μm. In some instances, the microcapsules have a size ranging from 0.001 μm to 0.01 μm, 0.002 μm to 0.01 μm, 0.003 μm to 0.01 μm, 0.004 μm to 0.01 μm, 0.005 to 0.01 μm, or 0.006 μm to 0.01 μm, or 0.007 μm to 0.01, or 0.008 μm to 0.01 μm, or 0.009 μm to 0.01 μm, or 0.005 μm to 0.003 μm, or 0.005 μm to 0.002 μm, or 0.005 μm to 0.001 μm. The size of the microcapsules may be measured as the largest dimension of the microcapsule (e.g., length, width, or height), or for spherical microcapsules (e.g., spherical surfaces), may be measured as the average diameter of the microcapsules. By "average" is meant the arithmetic mean. In some embodiments, the microcapsules have an average diameter of from 200 nm to 2 μm, such as 150 nm to 2 μm, 100 nm to 2 μm or 50 nm to 2 μm. In some embodiments, the microcapsules have an average diameter of from 1 nm to 200 nm. In certain instances, the microcapsules have an average size of 2 μm. In certain instances, the microcapsules have an average size of 5 μm. In certain instances, the microstructures have an average size of 10 μm. In certain instances, the microstructures have an average size of 20 μm. In certain instances, the microcapsule has an average size of 150 nm. In certain instances, the microcapsule has an average size of 200 nm. Mixtures of different sizes and/or shapes of self-assembled microcapsules may be used as desired. In other embodiments, the self-assembled microcapsules have substantially the same size and shape. In some cases, the microcapsule has a thickness of from 1% to 50% of the volume of the microcapsule, such as 1% to 40%, 1% to 30%, 1% to 20%, or 1% to 10%. By "thickness", it is meant the thickness of the shell.

The self-assembled microcapsules of the present disclosure are composed of stimuli-responsive organic ligand functionalized nanoparticles. In certain embodiments, the nanoparticles are stably associated with each other to form the shell. By "stably associated" is meant that a moiety is bound to or otherwise associated with another moiety or structure under standard conditions. In certain instances, the nanoparticles may be stably associated with each other such that the shell substantially maintains its shape after formation of the shell. In some embodiments, the nanoparticles are stably associated with each other through non-covalent interactions, such as, but not limited to, ionic bonds, hydrophobic interactions, hydrogen bonds, van der Waals forces (e.g., London dispersion forces), dipole-dipole interactions, π-π interactions and the like. In some embodiments, the nanoparticles are stably associated with each other through covalent bonds. For example, a nanoparticle may be covalently bound or cross-linked to one or more nanoparticles in the shell. In certain cases, the nanoparticles are stably associated with each other through a combination of non-covalent and covalent interactions.

As described above, the self-assembled microcapsules of the present disclosure may be composed of nanoparticles. The nanoparticles may have a size of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 90 nm or less, or 80 nm or less, or 70 nm or less, or 60 nm or less, or 50 nm or less, or 40 nm or less, or 30 nm or less, or 20 nm or less, or 10 nm or less, or 9 nm or less, or 8 nm or less, or 7 nm or less, or 6 nm or less, or 5 nm or less, or 4 nm or less, or 3 nm or less, or 2 nm or less, or 1 nm or less. In some instances, the nanoparticles have a size ranging from 0.1 nm to 1000 nm, such as from 0.5 nm to 1000 nm, or 1 nm to 1000 nm, or 1 nm to 900 nm, or 1 nm to 800 nm, or 1 nm to 700 nm, or 1 nm to 600 nm, or 1 nm to 500 nm, or 1 nm to 400 nm, or 1 nm to 300 nm, or 1 nm to 250 nm, or 1 nm to 200 nm, or 1 nm to 150 nm, or 1 nm to 100 nm, or 1 nm to 90 nm, or 1 nm to 80 nm, or 1 nm to 70 nm, or 1 nm to 60 nm, or 1 nm to 50 nm, or 1 nm to 40 nm, or 1 nm to 30 nm, or 1 nm to 20 nm, or 1 nm to 10 nm, or 1 nm to 9 nm, or 1 nm to 8 nm, or 1 nm to 7 nm, or 1 nm to 6 nm, or 1 nm to 5 nm. The size of the nanoparticles may be measured as the largest dimension of the nanoparticle (e.g., length, width, etc.), or for spherical nanoparticles, may be measured as the average diameter of the nanoparticles. In certain instances, the nanoparticles have an average size of 5 nm. In certain instances, the nanoparticles have an average size of 6 nm. Mixtures of different sizes and/or shapes of nanoparticles may be included in the three-dimensional structures as desired. In other embodiments, the nanoparticles have substantially the same size and shape.

Nanoparticles may have various shapes, such as, but not limited to, spherical, ellipsoid, cylinder, cone, cube, cuboid, pyramidal, needle, and the like. The nanoparticles may be made of any convenient material, such as, but not limited to, upconversion nanoparticles, plasmonic nanoparticles, or combinations thereof. The nanoparticles may be made of a semiconductor material, a metal, a metal oxide, a metal coated material, a metalloid, an oxide, a magnetic material, a nanosome, a lipidsome, a polymer, combinations thereof, and the like. For example, nanoparticles may be composed of materials, such as, but not limited to, titanium dioxide, silicon, gold, gold-plated silica, polymers, silver, zinc oxide, iron oxide, cobalt and the like. In some cases, the nanoparticles may be composed of coated nanoparticles, such as polymer-coated, gold coated, silver coated, zinc coated, graphene coated, graphene coated cobalt, silica coated iron oxide, silica coated cobalt nanoparticles, and the like. In some embodiments, the nanoparticles are gold nanoparticles. In other embodiments, the nanoparticles are non-metallic nanoparticles.

In certain embodiments, the nanoparticles that form the self-assembled microcapsule are arranged as a mixture of nanoparticles to form the three-dimensional structure. For instance, the microcapsule may be composed of a mixture (e.g., a substantially homogeneous mixture) of nanoparticles. In some embodiments, the nanoparticles are arranged in one or more layers to form the microcapsule. The composition of each layer of the microcapsule may be the same or may be different. For example, each layer of the microcapsule may be composed of the same type of nanoparticle or mixture of nanoparticles. Nanoparticles that are of the same type may include nanoparticles that are substantially the same with respect to their physical and chemical characteristics, such as, but not limited to, size, shape, composition, organic ligand attached to the surface of the nanoparticle, and the like. In other cases, a layer of the microcapsule may have a different composition (e.g., a different nanoparticle or mixture of nanoparticles) than an adjacent layer. For instance, nanoparticles may differ with respect to one or more physical and/or chemical characteristics, such as, but not limited to, size, shape, composition, organic ligand attached to the surface of the nanoparticle, and the like.

In certain embodiments, the self-assembled microcapsule is composed of nanoparticles where the nanoparticles are a mixture of different types of nanoparticles. For instance, the mixture of nanoparticles may be a heterogeneous mixture of nanoparticles that is composed of different types of nanoparticles. The different types of nanoparticles may include nanoparticles that vary in one or more physical and/or chemical characteristics, such as, but not limited to, size, shape, composition, organic ligand attached to the surface of the nanoparticle, combinations thereof, and the like.

In certain embodiments, the nanoparticle is composed of a material or mixture of materials, such that the composition of the nanoparticle is substantially homogeneous. In some cases, the nanoparticle is composed of two or more materials. Nanoparticles composed of two or more materials include nanoparticles composed of a mixture of the two or more materials, such that the nanoparticles have a substantially homogeneous composition, and nanoparticles where the nanoparticles are composed of regions of a material interspersed with or adjacent to regions of one or more different materials. For instance, a nanoparticle may be composed of a core of a first material (or mixture of materials) substantially surrounded by a shell of a different material (or different mixture of materials). The shell of the different material may be disposed as one or more layers of material on a surface of the core of the first material.

The nanoparticles of the present disclosure are organic ligand-functionalized nanoparticles. An organic ligand-functionalized nanoparticle is a nanoparticle that includes an organic ligand attached to the surface of the nanoparticle. The ligand may be attached to the surface of the nanoparticle through non-covalent interactions, such as, but not limited to, ionic bonds, hydrophobic interactions, hydrogen bonds, van der Waals forces (e.g., London dispersion forces), dipole-dipole interactions, π-π interactions and the like, or through covalent bonds. In certain embodiments, the ligand is attached to the surface of the nanoparticle through a covalent bond.

Organic ligands suitable for functionalization of the nanoparticles may vary depending on the desired properties of the functionalized nanoparticle. For example, the organic ligand on the ligand-functionalized nanoparticle may be selected such that the spacing between adjacent ligand-functionalized nanoparticles is a desired spacing. Stated another way, in some instances, the spacing between adjacent organic ligand-functionalized nanoparticles may depend on one or more properties of the organic ligand, such as, but not limited to, the size, structure, and/or orientation of the ligand. In some cases, the spacing between adjacent nanoparticles is 1 nm or more, such as 2 nm or more, 3 nm or more, 4 nm or more, 5 nm or more, 6 nm or more, or 7 nm or more, or 8 nm or more, 9 nm or more, 10 nm or more, 11 nm or more, 12 nm or more, 13 nm or more, 14 nm or more, 15 nm or more, 16 nm or more, 17 nm or more, 18 nm or more, 19 nm or more, or 20 nm or more. In some cases, the spacing between adjacent nanoparticles is 20 nm or more, such as 25 nm or more, 30 nm or more, 35 nm or more, 40 nm or more, 45 nm or more, 50 nm or more, 55 nm or more, 60 nm or more, 65 nm or more, 70 nm or more, 75 nm or more, 80 nm or more, 85 nm or more, 90 nm or more, 95 nm or more, 100 nm or more. In some cases, the spacing between adjacent nanoparticles is 10 nm or more. In some cases, the spacing between adjacent nanoparticles is 5 nm to 20 nm, such as 7 nm to 15 nm, or 10 nm to 15 nm. In some instances, the spacing between adjacent nanoparticles is 10 nm to 15 nm, such as 10 nm to 13 nm, or 10 nm to 12 nm. In some cases, the mean inter-particle separation of the nanoparticles is from 1 nm to 100 nm. In certain embodiments, the spacing between adjacent nanoparticles is selected so as to minimize shifts in the emission spectrum of the nanoparticles. In certain embodiments, the spacing between adjacent nanoparticles is selected so as to minimize energy losses due to fluorescence resonance energy transfer (FRET).

In some embodiments, the organic ligand disclosed herein has mesomorphic state properties, such as liquid crystalline properties. For instance, an organic ligand may include a rigid moiety and one or more flexible moieties. The rigid and flexible moieties of the organic ligands may facilitate alignment of the organic ligands in a common direction. For example, as described herein, organic ligand-functionalized nanoparticles may be dispersed in a mesomorphic material, such as a liquid crystalline liquid, and thus the flexible moiety may facilitate alignment of the organic ligand with the surrounding mesomorphic material. For instance, organic ligands attached to a surface of a nanoparticle may align with the director of a surrounding mesomorphic material (e.g., a nematic phase or mesomorphic state of the mesomorphic material).

In certain embodiments, the organic ligand has a phase transition temperature (also referred to as a melting temperature or clearing point) ranging from 50° C. to 150° C., such as 75° C. to 125° C., or 80° C. to 120° C., or 85° C. to 115° C., or 90° C. to 110° C. In certain embodiments, the organic ligand has a phase transition temperature (e.g., melting temperature or clearing point) of 100° C. For example, the phase transition temperature may be a temperature at which the organic ligand transitions from a first phase to a second phase (or vice versa). In some embodiments, the organic ligand may transition from a phase having positional order (e.g., an ordered spatial arrangement of the ligands, such as in an ordered lattice) or directional order (e.g., alignment of the ligands along a common directional axis) to a phase having substantially no positional or directional order. In some embodiments, the organic ligand may transition from a phase having substantially no positional or directional order to a phase having positional or directional order. In some cases, the organic ligand has positional and/or directional order below the phase transition temperature, and substantially no positional or directional order above the phase transition temperature. Similarly, organic ligands that are stably associated with or attached to a surface of organic ligand-functionalized nanoparticles may have a phase transition from a phase having substantially no positional or directional order to a phase having positional or directional order (or vice versa). As described above, organic ligands that are stably associated with or attached to a surface of organic ligand-functionalized nanoparticles may have a phase transition temperature (also referred to as a melting temperature or clearing point) ranging from 50° C. to 150° C., such as 75° C. to 125° C., or 80° C. to 120° C., or 85° C. to 115° C., or 90° C. to 110° C. In certain embodiments, organic ligands that are stably associated with or attached to a surface of organic ligand-functionalized nanoparticles may have a phase transition temperature (e.g., melting temperature or clearing point) of 100° C.

In certain embodiments, the organic ligands include aromatic rings. In certain cases, the organic ligands have a structure according to formulae (I), (IA), (II) or (IIA) or any of compounds (1) to (8) as described herein. In certain cases, the organic ligands have a bis(imino)pyridine core. In certain cases, the organic ligands have a mono(imino)pyridine core. In certain cases, the organic ligand is attached to the surface of the nanoparticle through a heteroatom, e.g., an imine nitrogen, pyridine nitrogen, or a tether including a thiol or amine group. In certain instances, the organic ligand is attached to the surface of the nanoparticle through more than one point of attachment, such as 2 points of attachment or more, 3 points of attachment or more, or even more. In some embodiments, organic ligands suitable for functionalization of the nanoparticles include substituted alkyl groups. In some cases, the subject self-assembled microcapsules include organic ligands octadecylamine (ODA), octadecylphosphonic acid, oleic acid, combinations thereof, and the like.

In certain embodiments, the organic ligand includes a cross-linkable functional group. The cross-linkable functional group may be a group that, when activated, can form an attachment to another moiety. In some cases, the attachment may attach an organic ligand to another organic ligand (e.g., an organic ligand of an adjacent organic ligand-functionalized nanoparticle), may attach an organic ligand to a nanoparticle, may attach an organic ligand comprising an aromatic group to an organic ligand comprising a substituted alkyl group. In certain embodiments, the cross-linkable functional group forms a covalent bond attachment the other moiety. In certain embodiments, the cross-linkable functional group is a light activated cross-linkable functional group. A light activated cross-linkable functional group is a cross-linkable functional group that may form an attachment to another moiety when light is applied to the light activated cross-linkable functional group. For example, exposure of the light activated cross-linkable functional group to light may activate the functional group, thus forming a reactive moiety capable of forming a crosslink to another moiety as described above. In some instances, the applied light is ultraviolet (UV) light. In some instances, the applied light is visible light. In some instances, the applied light is infrared light. For example, the applied light may be UV light having a wavelength ranging from 100 nm to 400 nm, such as 150 nm to 400 nm, or 200 nm to 400 nm, or 300 nm to 400 nm. In some instances, the applied UV light may be approximately 350 nm, such as 360 nm or 364 nm. Other types of cross-linkable functional groups may also be used, such as chemically activated cross-linkable functional groups, and the like.

Any convenient cross-linkable functional group may be used. In certain embodiments, the cross-linkable functional group is a functional group that, when activated, forms a reactive moiety. The reactive moiety may then react with another moiety (e.g., organic ligand, nanoparticle, etc.) to form an attachment (e.g., covalent bond) between the cross-linkable functional group and the other moiety. In some cases, the reactive moiety is a moiety capable of forming a covalent bond to carbon. For example, the reactive moiety may be a nitrene, such as a reactive nitrene derived from an azide functional group (e.g., an azide cross-linkable functional group). A nitrene may form a covalent bond to carbon to produce an amine or amide. In some instances, the cross-linkable functional group includes an azide, such as, but not limited to, a tetrafluoro-arylazide group.

In some embodiments, the stimuli-responsive organic ligand has a structure according to formula (I):

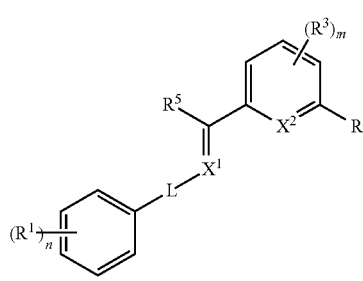

(I)

wherein:
  $X^1$ and $X^2$ are each independently selected from N and $CR^7$, wherein each $R^7$ is independently selected from H, halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
  L is a bond or a linker;
  $R^1$ and $R^3$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
  $R^2$ is selected from H, halogen, hydroxyl, azido, acyl, substituted acyl, imine, substituted imine, alkyl, substituted alkyl, alkenyl, substituted alkenyl, alkynyl, substituted alkynyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof
  $R^5$ is selected from H, alkyl, substituted alkyl, aryl, and substituted aryl;
  n is an integer from 0 to 5; and
  m is an integer from 0 to 3.

In some embodiments of formula (I), both $X^1$ and $X^2$ are N. In some embodiments, $X^1$ is $CR^7$ and $X^2$ is N. In other cases, $X^2$ is $CR^7$ and $X^2$ is N. In some cases, both $X^1$ and $X^2$ are $CR^7$. In certain cases, $R^7$ is H. In certain other cases, $R^7$ is alkyl or substituted alkyl.

In some instances of formula (I), $R^2$ is hydrogen. In some instances of formula (I), $R^2$ is halogen, e.g., bromide, fluoride, iodide or chloride. In some instances, $R^2$ group is hydroxyl. In some instances, $R^2$ is azido. In some instances, $R^2$ is alkynyl or substituted alkynyl. In some instances, $R^2$ is acyl or substituted acyl. In some instances, $R^2$ is amino or substituted amino. In some instances, $R^2$ is cycloalkyl or substituted cycloalkyl. In some instances, $R^2$ is heterocycloalkyl or substituted heterocycloalkyl. In some instances, $R^2$ is aryl or substituted aryl. In some instances, $R^2$ is heteroaryl or substituted heteroaryl. In some instances, $R^2$ group is phosphate or substituted phosphate. In some instances, $R^2$ group is phosphoryl or substituted phosphoryl. In some other instances, $R^2$ group is thiol or substituted thiol.

In some other instances of formula (I), $R^2$ group is alkyl or substituted alkyl. In certain instances, $R^2$ is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^2$ is $C_1$ alkyl, such as methyl. In some instances, $R^2$ is $C_2$ alkyl, such as ethyl. In some instances, $R^2$ is $C_3$ alkyl, such as propyl. In some instances, $R^2$ is $C_4$ alkyl, such as butyl. In some instances, $R^2$ is $C_5$ alkyl, such as pentyl. In some instances, $R^2$ is $C_6$ alkyl, such as hexyl. In some instances, the substituent on the substituted alkyl is selected from amine, thiol, phosphate or substituted phosphate.

In some instances of formula (I), $R^2$ group is alkenyl or substituted alkenyl. In certain instances, $R^2$ is $C_{1-12}$ alkenyl, such as $C_{1-10}$ alkenyl, $C_{1-8}$ alkenyl, $C_{1-8}$ alkenyl, or $C_{1-3}$ alkenyl, wherein any of the alkenyl groups are optionally substituted. In some instances, $R^2$ is $C_1$ alkenyl, such as methylene. In some instances, $R^2$ is $C_2$ alkenyl, such as ethylene. In some instances, $R^2$ is $C_3$ alkenyl, such as propene. In some instances, $R^2$ is $C_4$ alkenyl, such as butene. In some instances, $R^2$ is $C_5$ alkenyl, such as pentene. In some instances, $R^2$ is $C_6$ alkenyl, such as hexene. In some instances, the substituent on the substituted alkenyl is selected from amine, thiol, phosphate or substituted phosphate.

In some instances of formula (I), $R^2$ is alkoxy, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^2$ is $C_5$ alkoxy, such as pentyloxy. In some instances, $R^2$ is $C_4$ alkoxy, such as butyloxy. In some instances, $R^2$ is $C_1$ alkoxy, such as methoxy. In some instances, $R^2$ is $C_2$ alkoxy, such as ethoxy. In some instances, $R^2$ is substituted alkoxy, such as a substituted $C_{1-12}$ alkoxy, substituted $C_{1-10}$ alkoxy, substituted $C_{1-8}$ alkoxy, or substituted $C_{1-6}$ alkoxy. In some instances, $R^2$ is substituted $C_6$ alkoxy, such as substituted hexyloxy. In some instances, $R^2$ is substituted $C_{12}$ alkoxy, such as substituted dodecyloxy. In some instances, the substituent on the substituted alkoxy is selected from amine, thiol, phosphate or substituted phosphate.

In some instances of formula (I), $R^2$ is an imine, substituted imine. In some instances, the substituent on the substituted imine is selected from an alkyl, substituted alkyl, alkenyl, substituted alkenyl, aryl, substituted aryl, heteroaryl or substituted heteroaryl. In certain cases, the substituent on the substituted imine is an aryl or substituted aryl group. In certain embodiments, the substituted imine is of the formula (IB) or (IC):

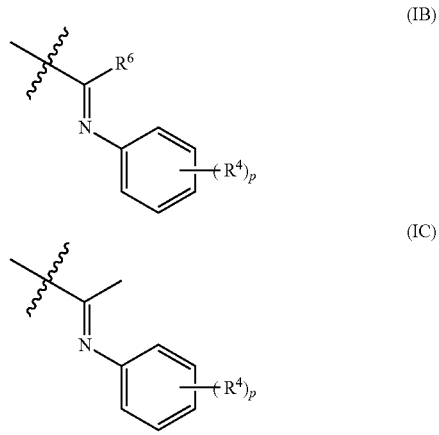

wherein, $R^6$, $R^4$ and p are as defined herein.

In some embodiments, the stimuli-responsive organic ligand of formula (I) has a structure according to formula (IA):

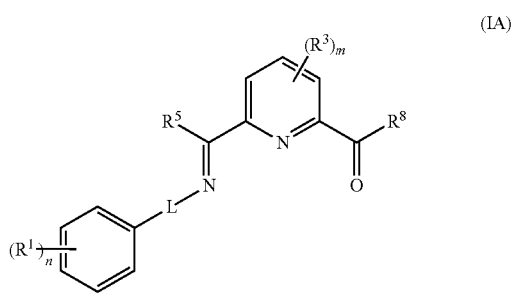

wherein:
L is a bond, or a linker;
$R^1$ and $R^3$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
$R^5$ and $R^8$ are each independently selected from H, alkyl, substituted alkyl, aryl, and substituted aryl;
n is an integer from 0 to 5; and
m is an integer from 0 to 3.

In some cases of formula (I) or (IA), L is a bond. In other cases of formula (I) or (IA), L is a linker. In certain cases, the linker is selected from alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, cycloalkyl, substituted cycloalkyl, heterocycloalkyl, substituted heterocycloalkyl, aryl, substituted aryl, heteroaryl and substituted heteroaryl. In some cases, L is a linker selected from alkyl and substituted alkyl. In some cases, L is a linker selected from alkenyl and substituted alkenyl. In some cases, L is a linker selected from alkynyl and substituted alkynyl. In some cases, L is a linker selected from acyl and substituted acyl. In some cases, L is a linker selected from $C_1$-$C_{12}$ alkoxy and substituted $C_1$-$C_{12}$ alkoxy. In some cases, L is a linker selected from cycloalkyl and substituted cycloalkyl. In some cases, L is a linker selected from heterocycloalkyl and substituted heterocycloalkyl. In some cases, L is a linker selected from aryl and substituted aryl. In some cases, L is a linker selected from heteroaryl and substituted heteroaryl. In some cases, the linker includes an amino, or a thiol group. In some cases, the linker is a polyalkene group.

In some instances of formula (I) or (IA), at least one $R^1$ group is halogen, e.g., bromide, fluoride, iodide or chloride. In some instances, at least one $R^1$ group is hydroxyl. In some instances, at least one $R^1$ group is azido. In some instances, at least one $R^1$ is alkynyl or substituted alkynyl. In some instances, at least one $R^1$ group is acyl or substituted acyl. In some instances, at least one $R^1$ group is amino or substituted amino. In some instances, at least one $R^1$ group is cycloalkyl or substituted cycloalkyl. In some instances, at least one $R^1$ group is heterocycloalkyl or substituted heterocycloalkyl. In some instances, at least one $R^1$ group is aryl or substituted aryl. In some instances, at least one $R^1$ group is heteroaryl or substituted heteroaryl. In some instances, at least one $R^1$ group is phosphate or substituted phosphate. In some instances, at least one $R^1$ group is phosphoryl or substituted phosphoryl. In some other instances, at least one $R^1$ group is thiol or substituted thiol.

In some other instances of formula (I) or (IA), at least one $R^1$ group is alkyl or substituted alkyl. In certain instances, at least one $R^1$ group is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^1$ is $C_1$ alkyl, such as methyl. In some instances, $R^1$ is $C_2$ alkyl, such as ethyl. In some instances, $R^1$ is $C_3$ alkyl, such as propyl. In some instances, $R^1$ is $C_4$ alkyl, such as butyl. In some instances, $R^1$ is $C_5$ alkyl, such as pentyl. In some instances, $R^1$ is $C_6$ alkyl, such as hexyl. In some instances, the substituent on the substituted alkyl is selected from amine, thiol, phosphate or substituted phosphate.

In some instances of formula (I) or (IA), at least one $R^1$ group is alkenyl or substituted alkenyl. In certain instances, at least one $R^1$ group is $C_{1-12}$ alkenyl, such as $C_{1-10}$ alkenyl, $C_{1-8}$ alkenyl, $C_{1-6}$ alkenyl, or $C_{1-3}$ alkenyl, wherein any of the alkenyl groups are optionally substituted. In some instances, $R^1$ is $C_1$ alkenyl, such as methylene. In some instances, $R^1$ is $C_2$ alkenyl, such as ethylene. In some instances, $R^1$ is $C_3$ alkenyl, such as propene. In some instances, $R^1$ is $C_4$ alkenyl, such as butene. In some instances, $R^1$ is $C_5$ alkenyl, such as pentene. In some instances, $R^1$ is $C_6$ alkenyl, such as hexene. In some instances, the substituent on the substituted alkenyl is selected from amine, thiol, phosphate or substituted phosphate.

In some instances of formula (I) or (IA), at least one $R^1$ group is alkoxy, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is $C_2$ alkoxy, such as ethoxy. In some instances, $R^1$ is substituted alkoxy, such as a substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is selected from amine, thiol, phosphate or substituted phosphate.

In certain embodiments of formula (I) or (IA), n is 0, such that the aromatic ring is not substituted with any $R^1$ groups. In other cases, n is greater than 0, such as 1, 2, 3, 4 or 5. In some cases, n is 1, such that the aromatic ring is substituted with one $R^1$ group. In some cases, n is 2, such that the aromatic ring is substituted with two $R^1$ groups. In some cases, n is 3, such that the aromatic ring is substituted with three $R^1$ groups. In some cases, n is 4, such that the aromatic ring is substituted with four $R^1$ groups. In some cases, n is 5, such that the aromatic ring is substituted with five $R^1$ groups. It will be understood that when n is greater than 1, the $R^1$ groups may be independently selected from any combination of the groups described herein.

In some instances of formula (I) or (IA), at least one $R^3$ group is halogen, e.g., bromide, fluoride, iodide or chloride. In some instances, at least one $R^3$ group is hydroxyl. In some instances, at least one $R^3$ group is azido. In some instances, at least one $R^3$ is alkynyl or substituted alkynyl. In some instances, at least one $R^3$ group is acyl or substituted acyl. In some instances, at least one $R^3$ group is amino or substituted amino. In some instances, at least one $R^3$ group is cycloalkyl or substituted cycloalkyl. In some instances, at least one $R^3$ group is heterocycloalkyl or substituted heterocycloalkyl. In some instances, at least one $R^3$ group is aryl or substituted aryl. In some instances, at least one $R^3$ group is heteroaryl or substituted heteroaryl. In some instances, at least one $R^3$ group is phosphate or substituted phosphate. In some instances, at least one $R^3$ group is phosphoryl or substituted phosphoryl. In some other instances, at least one $R^3$ group is thiol or substituted thiol.

In some other instances of formula (I) or (IA), at least one $R^3$ group is alkyl or substituted alkyl. In certain instances, at least one $R^3$ group is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^3$ is $C_1$ alkyl, such as methyl. In some instances, $R^3$ is $C_2$ alkyl, such as ethyl. In some instances, $R^3$ is $C_3$ alkyl, such as propyl. In some instances, $R^3$ is $C_4$ alkyl, such as butyl. In some instances, $R^3$ is $C_5$ alkyl, such as pentyl. In some instances, $R^3$ is $C_6$ alkyl, such as hexyl. In some instances, the substituent on the substituted alkyl is selected from amine, thiol, phosphate or substituted phosphate.

In some instances of formula (I) or (IA), at least one $R^3$ group is alkenyl or substituted alkenyl. In certain instances, at least one $R^3$ group is $C_{1-12}$ alkenyl, such as $C_{1-10}$ alkenyl, $C_{1-8}$ alkenyl, $C_{1-6}$ alkenyl, or $C_{1-3}$ alkenyl, wherein any of the alkenyl groups are optionally substituted. In some instances, $R^3$ is $C_1$ alkenyl, such as methylene. In some instances, $R^3$ is $C_2$ alkenyl, such as ethylene. In some instances, $R^3$ is $C_3$ alkenyl, such as propene. In some instances, $R^3$ is $C_4$ alkenyl, such as butene. In some instances, $R^3$ is $C_5$ alkenyl, such as pentene. In some instances, $R^3$ is $C_6$ alkenyl, such as hexene. In some instances, the substituent on the substituted alkenyl is selected from amine, thiol, phosphate or substituted phosphate.

In some instances of formula (I) or (IA), at least one $R^3$ group is alkoxy, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^3$ is $C_5$ alkoxy, such as pentyloxy. In some instances, $R^3$ is $C_4$ alkoxy, such as butyloxy. In some instances, $R^3$ is $C_1$ alkoxy, such as methoxy. In some instances, $R^3$ is $C_2$ alkoxy, such as ethoxy. In some instances, $R^3$ is substituted alkoxy, such as a substituted $C_{1-12}$ alkoxy, substituted $C_{1-10}$ alkoxy, substituted $C_{1-8}$ alkoxy, or substituted $C_{1-6}$ alkoxy. In some instances, $R^3$ is substituted $C_6$ alkoxy, such as substituted hexyloxy. In some instances, $R^3$ is substituted $C_{12}$ alkoxy, such as substituted dodecyloxy. In some instances, the substituent on the substituted alkoxy is selected from amine, thiol, phosphate or substituted phosphate.

In certain embodiments of formula (I) or (IA), m is 0, such that the aromatic ring, or pyridine ring, is not substituted with any $R^3$ groups. In other cases, m is greater than 0, such as 1, 2 or 3. In some cases, m is 1, such that the aromatic ring, or pyridine ring, is substituted with one $R^3$ group. In some cases, m is 2, such that the aromatic ring, or pyridine ring, is substituted with two $R^3$ groups. In some cases, m is 3, such that the aromatic ring, or pyridine ring, is substituted with three $R^3$ groups. It will be understood that when m is greater than 1, the $R^3$ groups may be independently selected from any combination of the groups described herein.

In some embodiments of formula (I) or (IA), $R^5$ is hydrogen. In other cases, $R^5$ is aryl. In yet other cases, $R^5$ is substituted aryl. In certain embodiments, $R^5$ is alkyl or substituted alkyl. In certain instances, $R^5$ is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^5$ is $C_1$ alkyl, such as methyl. In some instances, $R^5$ is $C_2$ alkyl, such as ethyl. In some instances, $R^5$ is $C_3$ alkyl, such as propyl. In some instances, $R^5$ is $C_4$ alkyl, such as butyl. In some instances, $R^5$ is $C_5$ alkyl, such as pentyl. In some instances, $R^5$ is $C_6$ alkyl, such as hexyl. In some instances, the substituent on the substituted alkyl is selected from amine, thiol, phosphate or substituted phosphate. In certain cases, $R^5$ is methyl.

In some embodiments of formula (IA), $R^8$ is hydrogen. In other cases, $R^8$ is aryl. In yet other cases, $R^8$ is substituted aryl. In certain embodiments, $R^8$ is alkyl or substituted alkyl. In certain instances, $R^8$ is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^8$ is $C_1$ alkyl, such as methyl. In some instances, $R^8$ is $C_2$ alkyl, such as ethyl. In some instances, $R^8$ is $C_3$ alkyl, such as propyl. In some instances, $R^8$ is $C_4$ alkyl, such as butyl. In some instances, $R^8$ is $C_5$ alkyl, such as pentyl. In some instances, $R^8$ is $C_6$ alkyl, such as hexyl. In some instances, the substituent on the substituted alkyl is selected from amine, thiol, phosphate or substituted phosphate.

In certain embodiments of formula (I) or (IA), n is 2 and each $R^1$ is an alkyl group. In certain cases, each $R^1$ is a methyl group. In certain cases, each $R^1$ is an ethyl group. In certain cases, each $R^1$ is an isopropyl group. In certain cases, each $R^1$ is a t-butyl group. In certain embodiments, both $R^1$ substituents are ortho substituents.

In certain embodiments of formula (I) or (IA), n is 1 and $R^1$ is an alkoxy group, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In certain embodiments, the alkoxy substituent is a para substituent.

In certain embodiments of formula (IA), both $R^5$ and $R^8$ are alkyl groups. In certain embodiments, the alkyl groups are both methyl groups. In other cases, $R^5$ and $R^8$ are each independently selected from methyl, ethyl, propyl, isopropyl, butyl, sec-butyl, tert-butyl, pentyl and hexyl.

In some embodiments, the stimuli-responsive organic ligand of formula (I) has a structure according to formula (II):

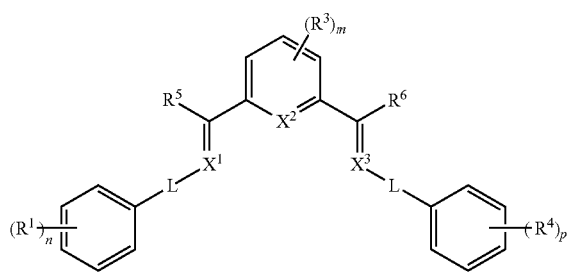

(II)

wherein
 $X^1$, $X^2$ and $X^3$ are each independently selected from N and $CR^7$, wherein each $R^7$ is independently selected from H, halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
 L is a bond, or a linker;
 $R^1$, $R^3$ and $R^4$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
 $R^5$ and $R^6$ are each independently selected from H, alkyl, substituted alkyl, aryl, and substituted aryl;
 n is an integer from 0 to 5;
 m is an integer from 0 to 3; and
 p is an integer from 0 to 5.

In some embodiments of formula (II), each of $X^1$, $X^2$ and $X^3$ are N. In some embodiments, $X^1$ is $CR^7$, $X^2$ is N and $X^3$ is N. In other cases, $X^2$ is $CR^7$, $X^1$ is N and $X^3$ is N. In other cases, $X^3$ is $CR^7$, $X^1$ is N and $X^2$ is N. In some embodiments, $X^1$ is $CR^7$, $X^2$ is $CR^7$ and $X^3$ is N. In other cases, $X^2$ is $CR^7$, $X^3$ is $CR^7$ and $X^1$ is N. In other cases, $X^3$ is $CR^7$, $X^1$ is $CR^7$ and $X^2$ is N. In some cases, each of $X^1$, $X^2$ and $X^3$ are $CR^7$. In certain cases, $R^7$ is H. In certain other cases, $R^7$ is alkyl or substituted alkyl.

In some embodiments, the stimuli-responsive organic ligand of formula (II) has a structure according to formula (IIA):

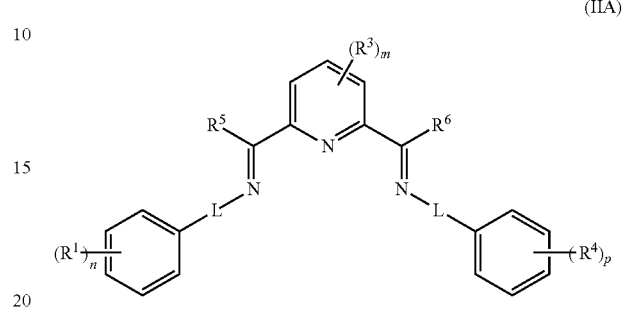

(IIA)

wherein:
 L is a bond or a linker;
 $R^1$, $R^3$ and $R^4$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
 $R^5$ and $R^6$ are each independently selected from H, alkyl, substituted alkyl, aryl, and substituted aryl;
 n is an integer from 0 to 5;
 m is an integer from 0 to 3; and
 p is an integer from 0 to 5.

In some cases of formula (II) or (IIA), L is a bond. In other cases of formula (II) or (IIA), L is a linker. In certain cases, the linker is selected from alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, cycloalkyl, substituted cycloalkyl, heterocycloalkyl, substituted heterocycloalkyl, aryl, substituted aryl, heteroaryl and substituted heteroaryl. In some cases, L is a linker selected from alkyl and substituted alkyl. In some cases, L is a linker selected from alkenyl and substituted alkenyl. In some cases, L is a linker selected from alkynyl and substituted alkynyl. In some cases, L is a linker selected from acyl and substituted acyl. In some cases, L is a linker selected from $C_1$-$C_{12}$ alkoxy and substituted $C_1$-$C_{12}$ alkoxy. In some cases, L is a linker selected from cycloalkyl and substituted cycloalkyl. In some cases, L is a linker selected from heterocycloalkyl and substituted heterocycloalkyl. In some cases, L is a linker selected from aryl and substituted aryl. In some cases, L is a linker selected from heteroaryl and substituted heteroaryl. In some cases, the linker includes an amino, or a thiol group. In some cases, the linker is a polyalkene group.

In some instances of formula (II) or (IIA), at least one $R^1$ group is halogen, e.g., bromide, fluoride, iodide or chloride. In some instances, at least one $R^1$ group is hydroxyl. In some instances, at least one $R^1$ group is azido. In some instances, at least one $R^1$ is alkynyl or substituted alkynyl. In some instances, at least one $R^1$ group is acyl or substituted acyl. In some instances, at least one $R^1$ group is amino or substituted amino. In some instances, at least one $R^1$ group is cycloalkyl or substituted cycloalkyl. In some instances, at least one $R^1$ group is heterocycloalkyl or substituted heterocycloalkyl. In some instances, at least one $R^1$ group is aryl or substituted aryl. In some instances, at least one $R^1$ group is heteroaryl or substituted heteroaryl. In some instances, at least one $R^1$ group is phosphate or substituted phosphate. In some instances, at least one $R^1$ group is phosphoryl or substituted phosphoryl. In some other instances, at least one $R^1$ group is thiol or substituted thiol.

In some other instances of formula (II) or (IIA), at least one $R^1$ group is alkyl or substituted alkyl. In certain instances, at least one $R^1$ group is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^1$ is $C_1$ alkyl, such as methyl. In some instances, $R^1$ is $C_2$ alkyl, such as ethyl. In some instances, $R^1$ is $C_3$ alkyl, such as propyl. In some instances, $R^1$ is $C_4$ alkyl, such as butyl. In some instances, $R^1$ is $C_5$ alkyl, such as pentyl. In some instances, $R^1$ is $C_6$ alkyl, such as hexyl. In some instances, the substituent on the substituted alkyl is selected from amine, thiol, phosphate or substituted phosphate.

In some instances of formula (II) or (IIA), at least one $R^1$ group is alkenyl or substituted alkenyl. In certain instances, at least one $R^1$ group is $C_{1-12}$ alkenyl, such as $C_{1-10}$ alkenyl, $C_{1-8}$ alkenyl, $C_{1-6}$ alkenyl, or $C_{1-3}$ alkenyl, wherein any of the alkenyl groups are optionally substituted. In some instances, $R^1$ is $C_1$ alkenyl, such as methylene. In some instances, $R^1$ is $C_2$ alkenyl, such as ethylene. In some instances, $R^1$ is $C_3$ alkenyl, such as propene. In some instances, $R^1$ is $C_4$ alkenyl, such as butene. In some instances, $R^1$ is $C_5$ alkenyl, such as pentene. In some instances, $R^1$ is $C_6$ alkenyl, such as hexene. In some instances, the substituent on the substituted alkenyl is selected from amine, thiol, phosphate or substituted phosphate.

In some instances of formula (II) or (IIA), at least one $R^1$ group is alkoxy, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ is $C_5$ alkoxy, such as pentyloxy. In some instances, $R^1$ is $C_4$ alkoxy, such as butyloxy. In some instances, $R^1$ is $C_1$ alkoxy, such as methoxy. In some instances, $R^1$ is $C_2$ alkoxy, such as ethoxy. In some instances, $R^1$ is substituted alkoxy, such as a substituted $C_{1-12}$ alkoxy, substituted $C_{1-10}$ alkoxy, substituted $C_{1-8}$ alkoxy, or substituted $C_{1-6}$ alkoxy. In some instances, $R^1$ is substituted $C_6$ alkoxy, such as substituted hexyloxy. In some instances, $R^1$ is substituted $C_{12}$ alkoxy, such as substituted dodecyloxy. In some instances, the substituent on the substituted alkoxy is selected from amine, thiol, phosphate or substituted phosphate.

In certain embodiments of formula (II) or (IIA), n is 0, such that the aromatic ring is not substituted with any $R^1$ groups. In other cases, n is greater than 0, such as 1, 2, 3, 4 or 5. In some cases, n is 1, such that the aromatic ring is substituted with one $R^1$ group. In some cases, n is 2, such that the aromatic ring is substituted with two $R^1$ groups. In some cases, n is 3, such that the aromatic ring is substituted with three $R^1$ groups. In some cases, n is 4, such that the aromatic ring is substituted with four $R^1$ groups. In some cases, n is 5, such that the aromatic ring is substituted with five $R^1$ groups. It will be understood that when n is greater than 1, the $R^1$ groups may be independently selected from any combination of the groups described herein.

In some instances of formula (II) or (IIA), at least one $R^3$ group is halogen, e.g., bromide, fluoride, iodide or chloride. In some instances, at least one $R^3$ group is hydroxyl. In some instances, at least one $R^3$ group is azido. In some instances, at least one $R^3$ is alkynyl or substituted alkynyl. In some instances, at least one $R^3$ group is acyl or substituted acyl. In some instances, at least one $R^3$ group is amino or substituted amino. In some instances, at least one $R^3$ group is cycloalkyl or substituted cycloalkyl. In some instances, at least one $R^3$ group is heterocycloalkyl or substituted heterocycloalkyl. In some instances, at least one $R^3$ group is aryl or substituted aryl. In some instances, at least one $R^3$ group is heteroaryl or substituted heteroaryl. In some instances, at least one $R^3$ group is phosphate or substituted phosphate. In some instances, at least one $R^3$ group is phosphoryl or substituted phosphoryl. In some other instances, at least one $R^3$ group is thiol or substituted thiol.

In some other instances of formula (II) or (IIA), at least one $R^3$ group is alkyl or substituted alkyl. In certain instances, at least one $R^3$ group is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^3$ is $C_1$ alkyl, such as methyl. In some instances, $R^3$ is $C_2$ alkyl, such as ethyl. In some instances, $R^3$ is $C_3$ alkyl, such as propyl. In some instances, $R^3$ is $C_4$ alkyl, such as butyl. In some instances, $R^3$ is $C_5$ alkyl, such as pentyl. In some instances, $R^3$ is $C_6$ alkyl, such as hexyl. In some instances, the substituent on the substituted alkyl is selected from amine, thiol, phosphate or substituted phosphate.

In some instances of formula (II) or (IIA), at least one $R^3$ group is alkenyl or substituted alkenyl. In certain instances, at least one $R^3$ group is $C_{1-12}$ alkenyl, such as $C_{1-10}$ alkenyl, $C_{1-8}$ alkenyl, $C_{1-6}$ alkenyl, or $C_{1-3}$ alkenyl, wherein any of the alkenyl groups are optionally substituted. In some instances, $R^3$ is $C_1$ alkenyl, such as methylene. In some instances, $R^3$ is $C_2$ alkenyl, such as ethylene. In some instances, $R^3$ is $C_3$ alkenyl, such as propene. In some instances, $R^3$ is $C_4$ alkenyl, such as butene. In some instances, $R^3$ is $C_5$ alkenyl, such as pentene. In some instances, $R^3$ is $C_6$ alkenyl, such as hexene. In some instances, the substituent on the substituted alkenyl is selected from amine, thiol, phosphate or substituted phosphate.

In some instances of formula (II) or (IIA), at least one $R^3$ group is alkoxy, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^3$ is $C_5$ alkoxy, such as pentyloxy. In some instances, $R^3$ is $C_4$ alkoxy, such as butyloxy. In some instances, $R^3$ is $C_1$ alkoxy, such as methoxy. In some instances, $R^3$ is $C_2$ alkoxy, such as ethoxy. In some instances, $R^3$ is substituted alkoxy, such as a substituted $C_{1-12}$ alkoxy, substituted $C_{1-10}$ alkoxy, substituted $C_{1-8}$ alkoxy, or substituted $C_{1-6}$ alkoxy. In some instances, $R^3$ is substituted $C_6$ alkoxy, such as substituted hexyloxy. In some instances, $R^3$ is substituted $C_{12}$ alkoxy, such as substituted dodecyloxy. In some instances, the substituent on the substituted alkoxy is selected from amine, thiol, phosphate or substituted phosphate.

In certain embodiments of formula (II) or (IIA), m is 0, such that the aromatic ring, or pyridine ring, is not substituted with any $R^3$ groups. In other cases, m is greater than 0, such as 1, 2 or 3. In some cases, m is 1, such that the aromatic ring, or pyridine ring, is substituted with one $R^3$ group. In some cases, m is 2, such that the aromatic ring, or pyridine ring, is substituted with two $R^3$ groups. In some cases, m is 3, such that the aromatic ring, or pyridine ring, is substituted with three $R^3$ groups. It will be understood that when m is greater than 1, the $R^3$ groups may be independently selected from any combination of the groups described herein.

In some instances of formula (II) or (IIA), at least one $R^4$ group is halogen, e.g., bromide, fluoride, iodide or chloride. In some instances, at least one $R^4$ group is hydroxyl. In some instances, at least one $R^4$ group is azido. In some instances, at least one $R^4$ is alkynyl or substituted alkynyl. In some instances, at least one $R^4$ group is acyl or substituted acyl. In some instances, at least one $R^4$ group is amino or substituted amino. In some instances, at least one $R^4$ group is cycloalkyl or substituted cycloalkyl. In some instances, at least one $R^4$ group is heterocycloalkyl or substituted heterocycloalkyl. In some instances, at least one $R^4$ group is aryl or substituted aryl. In some instances, at least one $R^4$ group is heteroaryl or substituted heteroaryl. In some instances, at least one $R^4$ group is phosphate or substituted phosphate. In some instances, at least one $R^4$ group is phosphoryl or substituted phosphoryl. In some other instances, at least one $R^4$ group is thiol or substituted thiol.

In some other instances of formula (II) or (IIA), at least one $R^4$ group is alkyl or substituted alkyl. In certain instances, at least one $R^4$ group is $C_{1-12}$ alkyl, such as $C_{1-10}$ alkyl, $C_{1-8}$ alkyl, $C_{1-6}$ alkyl, or $C_{1-3}$ alkyl, wherein any of the alkyl groups are optionally substituted. In some instances, $R^4$ is $C_1$ alkyl, such as methyl. In some instances, $R^4$ is $C_2$ alkyl, such as ethyl. In some instances, $R^4$ is $C_3$ alkyl, such as propyl. In some instances, $R^4$ is $C_4$ alkyl, such as butyl. In some instances, $R^4$ is $C_5$ alkyl, such as pentyl. In some instances, $R^4$ is $C_6$ alkyl, such as hexyl. In some instances, the substituent on the substituted alkyl is selected from amine, thiol, phosphate or substituted phosphate.

In some instances of formula (II) or (IIA), at least one $R^4$ group is alkenyl or substituted alkenyl. In certain instances, at least one $R^4$ group is $C_{1-12}$ alkenyl, such as $C_{1-10}$ alkenyl, $C_{1-8}$ alkenyl, $C_{1-6}$ alkenyl, or $C_{1-3}$ alkenyl, wherein any of the alkenyl groups are optionally substituted. In some instances, $R^4$ is $C_1$ alkenyl, such as methylene. In some instances, $R^4$ is $C_2$ alkenyl, such as ethylene. In some instances, $R^4$ is $C_3$ alkenyl, such as propene. In some instances, $R^4$ is $C_4$ alkenyl, such as butene. In some instances, $R^4$ is $C_5$ alkenyl, such as pentene. In some instances, $R^4$ is $C_6$ alkenyl, such as hexene. In some instances, the substituent on the substituted alkenyl is selected from amine, thiol, phosphate or substituted phosphate.

In some instances of formula (II) or (IIA), at least one $R^4$ group is alkoxy, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^4$ is $C_5$ alkoxy, such as pentyloxy. In some instances, $R^4$ is $C_4$ alkoxy, such as butyloxy. In some instances, $R^4$ is $C_1$ alkoxy, such as methoxy. In some instances, $R^4$ is $C_2$ alkoxy, such as ethoxy. In some instances, $R^4$ is substituted alkoxy, such as a substituted $C_{1-12}$ alkoxy, substituted $C_{1-10}$ alkoxy, substituted $C_{1-8}$ alkoxy, or substituted $C_{1-6}$ alkoxy. In some instances, $R^4$ is substituted $C_6$ alkoxy, such as substituted hexyloxy. In some instances, $R^4$ is substituted $C_{12}$ alkoxy, such as substituted dodecyloxy. In some instances, the substituent on the substituted alkoxy is selected from amine, thiol, phosphate or substituted phosphate.

In certain embodiments of formula (II) or (IIA), p is 0, such that the aromatic ring is not substituted with any $R^4$ groups. In other cases, p is greater than 0, such as 1, 2, 3, 4 or 5. In some cases, p is 1, such that the aromatic ring is substituted with one $R^4$ group. In some cases, p is 2, such that the aromatic ring is substituted with two $R^4$ groups. In some cases, p is 3, such that the aromatic ring is substituted with three $R^4$ groups. In some cases, p is 4, such that the aromatic ring is substituted with four $R^4$ groups. In some cases, p is 5, such that the aromatic ring is substituted with five $R^4$ groups. It will be understood that when p is greater than 1, the $R^4$ groups may be independently selected from any combination of the groups described herein.

In certain instances of formula (II) or (IIA), one or more of $R^1$, $R^3$ and $R^4$ are selected from $C_1$-$C_8$ alkoxy substituted with an amine, a thiol or hydroxyl group, and $C_1$-$C_8$ alkyl substituted with an amine, thiol or hydroxyl group.

In certain cases, $R^1$ is selected from $-O(CH_2)_qNH_2$, $-O(CH_2)_qSH$, $-O(CH_2)_qOH$, $-(CH_2)_qNH_2$, $-(CH_2)_qSH$ and $-(CH_2)_qOH$, wherein each q is independently an integer from 1 to 8. In certain cases, $R^1$ is $-O(CH_2)_qNH_2$, wherein q is independently an integer from 1 to 8. In certain cases, $R^1$ is $-O(CH_2)_qSH$, wherein q is independently an integer from 1 to 8. In certain cases, $R^1$ is $-O(CH_2)_qOH$, wherein q is independently an integer from 1 to 8. In certain cases, $R^1$ is $-(CH_2)_qNH_2$, wherein q is independently an integer from 1 to 8. In certain cases, $R^1$ is $-(CH_2)_qSH$, wherein q is independently an integer from 1 to 8. In certain cases, $R^1$ is $-(CH_2)_qOH$, wherein q is independently an integer from 1 to 8.

In certain cases, $R^3$ is selected from $-O(CH_2)_qNH_2$, $-O(CH_2)_qSH$, $-O(CH_2)_qOH$, $-(CH_2)_qNH_2$, $-(CH_2)_qSH$ and $-(CH_2)_qOH$, wherein each q is independently an integer from 1 to 8. In certain cases, $R^3$ is $-O(CH_2)_qNH_2$, wherein q is independently an integer from 1 to 8. In certain cases, $R^3$ is $-O(CH_2)_qSH$, wherein q is independently an integer from 1 to 8. In certain cases, $R^3$ is $-O(CH_2)_qOH$, wherein q is independently an integer from 1 to 8. In certain cases, $R^3$ is $-(CH_2)_qNH_2$, wherein q is independently an integer from 1 to 8. In certain cases, $R^3$ is $-(CH_2)_qSH$, wherein q is independently an integer from 1 to 8. In certain cases, $R^3$ is $-(CH_2)_qOH$, wherein q is independently an integer from 1 to 8.

In certain cases, $R^4$ is selected from $-O(CH_2)_qNH_2$, $-O(CH_2)_qSH$, $-O(CH_2)_qOH$, $-(CH_2)_qNH_2$, $-(CH_2)_qSH$ and $-(CH_2)_qOH$, wherein each q is independently an integer from 1 to 8. In certain cases, $R^4$ is $-O(CH_2)_qNH_2$, wherein q is independently an integer from 1 to 8. In certain cases, $R^4$ is $-O(CH_2)_qSH$, wherein q is independently an integer from 1 to 8. In certain cases, $R^4$ is $-O(CH_2)_qOH$, wherein q is independently an integer from 1 to 8. In certain cases, $R^4$ is $-(CH_2)_qNH_2$, wherein q is independently an integer from 1 to 8. In certain cases, $R^4$ is $-(CH_2)_qSH$, wherein q is independently an integer from 1 to 8. In certain cases, $R^4$ is $-(CH_2)_qOH$, wherein q is independently an integer from 1 to 8.

In certain embodiments of formula (II) or (IIA), both $R^5$ and $R^6$ are alkyl groups. In certain embodiments, the alkyl groups are both methyl groups. In other cases, $R^5$ and $R^8$ are each independently selected from methyl, ethyl, propyl, isopropyl, butyl, sec-butyl, tert-butyl, pentyl and hexyl.

In certain embodiments of formula (II) or (IIA), n and p are each 2 and each $R^1$ and $R^4$ are alkyl groups. In certain cases, $R^1$ and $R^4$ are each independently alkyl groups selected from methyl, ethyl, propyl, isopropyl, butyl, sec-butyl, tert-butyl, pentyl and hexyl. In certain other cases, each $R^1$ and $R^4$ are the same alkyl groups, wherein the alkyl groups are selected from methyl, ethyl, propyl, isopropyl, butyl, sec-butyl, tert-butyl, pentyl and hexyl. In certain cases, each of the $R^1$ and $R^4$ alkyl groups are methyl groups. In certain cases, each of the $R^1$ and $R^4$ alkyl groups are ethyl groups. In certain cases, each of the $R^1$ and $R^4$ alkyl groups are isopropyl groups. In certain cases, each of the $R^1$ and $R^4$ alkyl groups are t-butyl groups. In certain embodiments, both $R^1$ substituents are ortho substituents.

In certain embodiments of formula (II) or (IIA), n and p are each 1 and $R^1$ and $R^4$ are each alkoxy group, such as $C_{1-12}$ alkoxy, $C_{1-10}$ alkoxy, $C_{1-8}$ alkoxy, $C_{1-6}$ alkoxy, or $C_{1-3}$ alkoxy. In some instances, $R^1$ and $R^4$ are $C_5$ alkoxy, such as pentyloxy. In some instances, $R^1$ and $R^4$ are $C_4$ alkoxy, such as butyloxy. In some instances, $R^1$ and $R^4$ are $C_1$ alkoxy, such as methoxy. In certain embodiments, each alkoxy substituent is a para substituent.

In certain embodiments of formulae (I), (IA), (II) or (IIA), the organic ligand is selected from:

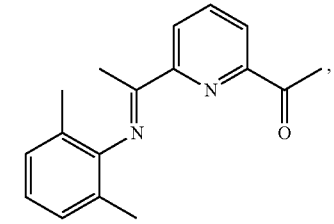

(1)

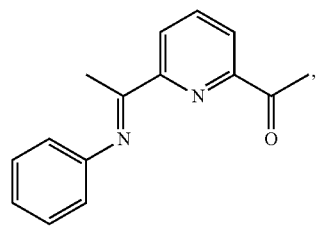

(2)

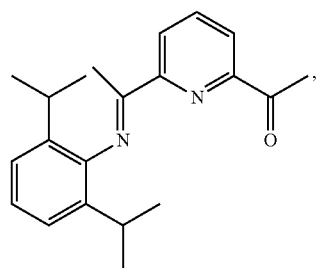

(3)

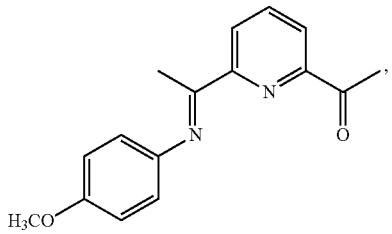

(4)

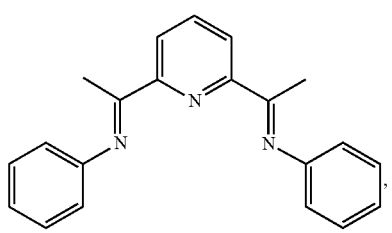

(5)

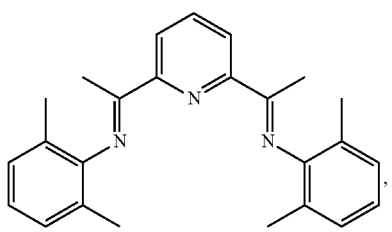

(6)

-continued

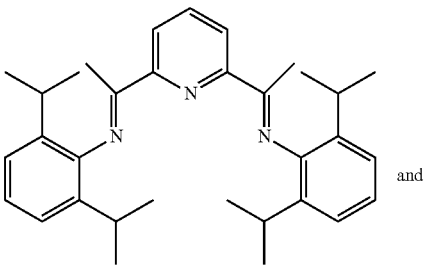

(7)

and

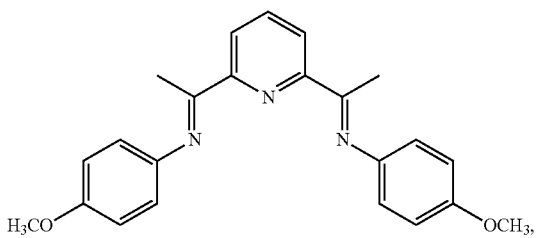

(8)

and combinations thereof.

As described above, the self-assembled microcapsules may be composed of nanoparticles having substantially the same physical and chemical characteristics, or in other embodiments, may be composed of nanoparticles having different physical and/or chemical characteristics. For example, physical and/or chemical characteristics of the nanoparticles that may be the same or may vary as described above may include, but are not limited to, size, shape, composition, ligand attached to the surface of the nanoparticle, organic ligand attached to the surface of the nanoparticle, cross-linkable functional group, combinations thereof, and the like. For instance, a nanoparticle may include a plurality of organic ligands attached to the surface of the nanoparticle, where the ligands are substantially the same. In other instances, the nanoparticle may include a plurality of ligands attached to the surface of the nanoparticle, where the ligands are different (e.g., ligands having different chemical structures and/or functional groups, such as cross-linkable functional groups as described herein). For example, combinations of various ligands may be attached to the surface of the same nanoparticle.

In some embodiments, the organic ligands undergo electron transfer upon activation with one or more external stimulus to produce a nanomaterial with openings. The term "openings" or "nanomaterial with openings" as used herein describes a nanomaterial structure which does not completely enclose a space or material. A nanomaterial with openings includes a surface that partially includes one or more voids or holes. An opening may be formed in a subject microcapsule to partially or completely release an enclosed material. For instance, an opening may be formed as a hole or void in a nanomaterial, such as to expose or release 50% or more of the space or material, or 60% or more, or 70% or more, or 80% or more, or 90% or more, or 95% or more, or 97% or more, or 99% or more of the space or material, such as 100% of the space or material. A nanomaterial with openings includes embodiments where the surface is substantially contiguous and has one or more voids (e.g., holes) in the surface, and also includes embodiments where the surface is substantially continuous, but the surface includes an opening such that that it does not extend to completely enclose the space or material.

Surfaces of a nanomaterial with openings may have various shapes and sizes. For instance, the openings include, but are not limited to, regular shapes such as spherical shells, ellipsoid shells, cylinder shells, cone shells, cube shells, cuboid shells, pyramidal shells, torus shells, and the like. In other embodiments, the opening may have an irregular shape. In certain embodiments, structures of the present disclosure have a shell configuration with openings, where the shell configuration is a spherical surface (i.e., a spherical shell) including one or more holes or voids. For example, a void or hole may have a size (e.g., largest dimension) of 100 µm or less, such as a size ranging from 100 nm to 100 µm (0.1 µm to 100 µm), 1 nm to 100 nm (0.001 µm to 0.1 µm).

In certain embodiments, after activation with one or more external stimulus a nanomaterial is produced with one or more openings, as described above, wherein the openings have a size of 1000 µm or less, such as 950 µm or less, or 900 µm or less, or 850 µm or less, or 800 µm or less, or 750 µm or less, or 700 µm or less, or 650 µm or less, or 600 µm or less, or 550 µm or less, or 500 µm or less, or 450 µm or less, or 400 µm or less, or 350 µm or less, or 300 µm or less, or 250 µm or less, or 200 µm or less, or 150 µm or less, or 100 µm or less, or 90 µm or less, or 80 µm or less, or 70 µm or less, or 60 µm or less, or 50 µm or less, or 40 µm or less, or 30 µm or less, or 20 µm or less, or 10 µm or less, or 9 µm or less, or 8 µm or less, or 7 µm or less, or 6 µm or less, or 5 µm or less, or 4 µm or less, or 3 µm or less, or 2 µm or less, or 1 µm or less, or 0.75 µm or less, or 0.5 µm or less, or 0.25 µm or less, or 0.1 µm or less, or 0.075 µm or less, or 0.05 µm or less, or 0.025 µm or less, or 0.01 µm or less. In some instances, the openings have a size ranging from 0.01 µm to 1000 µm, 0.025 µm to 1000 µm, 0.05 µm to 1000 µm, 0.075 µm to 1000 µm, 0.1 µm to 1000 µm, such as from 0.25 µm to 1000 µm, or 0.5 µm to 1000 µm, or 0.5 µm to 900 µm, or 0.5 µm to 800 µm, or 0.5 µm to 700, or 0.5 µm to 600 µm, or 0.5 µm to 500 µm, or 0.5 µm to 400 µm, or 0.5 µm to 300 µm, or 0.5 µm to 250 µm, or 0.5 µm to 200 µm, or 0.5 µm to 150 µm, or 0.5 µm to 100 µm, or 0.5 µm to 90 µm, or 0.5 µm to 80 µm, or 0.5 µm to 70 µm, or 0.5 µm to 60 µm, or 0.5 µm to 50 µm, or 0.5 µm to 40 µm, or 0.5 µm to 30 µm, or 0.5 µm to 20 µm, or 0.5 µm to 10 µm, or 0.5 µm to 9 µm, or 0.5 µm to 8 µm, or 0.5 µm to 7 µm, or 0.5 µm to 6 µm, or 0.5 µm to 5 µm, or 0.5 µm to 4 µm, or 0.5 µm to 3 µm, or 0.5 µm to 2 µm, or 0.5 µm to 1 µm. In some instances, the openings have a size ranging from 0.001 µm to 0.01 µm, 0.002 µm to 0.01 µm, 0.003 µm to 0.01 µm, 0.004 µm to 0.01 µm, 0.005 to 0.01 µm, or 0.006 µm to 0.01 µm, or 0.007 µm to 0.01, or 0.008 µm to 0.01 µm, or 0.009 µm to 0.01 µm, or 0.005 µm to 0.003 µm, or 0.005 µm to 0.002 µm, or 0.005 µm to 0.001 µm. The size of the openings may be measured as the largest dimension of the opening (e.g., length, width, or height), or for openings in a spherical shell (e.g., spherical surface), may be measured as the average diameter of the opening. By "average" is meant the arithmetic mean. In some embodiments, the nanomaterial includes one or more spherical openings having an average diameter of from 200 nm to 2 µm, such as 150 nm to 2 µm, 100 nm to 2 µm or 50 nm to 2 µm. In some embodiments, the openings have an average diameter of from 1 nm to 200 nm. In certain instances, the openings have an average size of 2 µm. In certain instances, the openings have an average size of 5 µm. In certain instances, the openings have an average size of 10 µm. In certain instances, the openings have an average size of 20 µm. In certain instances, the opening has an average size of 150 nm. In certain instances, the opening has an average size of 200 nm. Mixtures of different sizes and/or shapes of openings may be formed upon activation with an external stimulus. In other embodiments, openings may have substantially the same size and shape. In some cases, the opening has the same thickness as the self-assembled microcapsule. In some cases, the opening has a thickness of from 1% to 50% of the volume of the microcapsule, such as 1% to 40%, 1% to 30%, 1% to 20%, or 1% to 10%. By "thickness", it is meant the thickness of the shell.

Compositions

As described above, self-assembled microcapsules of the present disclosure may have a shell configuration that partially or completely encloses a space or material. In certain embodiments, the shell encloses a substrate, such as an active agent or live cells. In some instances, the active agent is a drug. Encapsulation of the active agent or live cells inside the microcapsule may facilitate one or more of: delivery of the active agent or live cells to a desired site; formulation of the active agent or live cells into a desired formulation; increased stability of the active agent or live cells; controlled release of the active agent or live cells; delayed release of the active agent or live cells; and the like. In certain cases, the substrate is released from the self-assembled microcapsule upon activation with an external stimulus. In certain cases, the external stimulus is an electrical input. In certain cases, the external stimulus is sound energy. In certain embodiments, full release of the encapsulated substrate is obtained in 5 minutes or less from the time of activation with the external stimulus. It will be understood that any convenient external stimulus capable of releasing an encapsulated substrate from a subject self-assembled microcapsule, at a targeted site in an individual without damaging living tissue, may find use in the subject methods. Examples of external stimulus and the method of releasing an encapsulated substrate from the subject self-assembled microcapsules will be described in more detail below.

Aspects of the present disclosure include compositions that include the self-assembled microcapsules as disclosed herein. The composition may include the self-assembled microcapsule and a liquid. In some instances, the composition includes the self-assembled microcapsule with a substrate encapsulated within dispersed in the liquid. In some instances, the liquid is a liquid crystalline fluid (e.g., a liquid crystalline liquid), such as a liquid crystalline liquid as described in more detail below. In some instances, the liquid is a solvent. In some embodiments the liquid is a pharmaceutically acceptable liquid. Any convenient solvent may be used, depending on the desired composition of the self-assembled microcapsule. Examples of solvents include, but are not limited to, organic solvents, such as toluene, dimethylbenzene, methylisopropylbenzene, methanol, ethyl acetate, chloroform, mixtures thereof, and the like. In some instances, the solvent is toluene.

Aspects of the present disclosure also include compositions for producing a self-assembled microcapsule of stably associated organic ligand-functionalized nanoparticles described herein. In certain embodiments, the composition includes stimuli-responsive organic ligand-functionalized nanoparticles and an anisotropic host phase (e.g., a liquid crystalline liquid). The nanoparticles in the composition for producing the self-assembled microcapsules may be any of the nanoparticles as described herein. For instance, the nanoparticles may be organic ligand-functionalized gold nanoparticles, as described herein. Alternatively, the nanoparticles may be organic ligand-functionalized non-metallic nanoparticles, as described herein.

In certain cases, the composition includes a liquid crystalline fluid (e.g., a liquid crystalline liquid). The liquid crystalline fluid may be composed of a liquid crystal. In certain cases, the liquid crystal has a phase transition, such as a phase transition between an isotropic phase and a nematic phase (or vice versa). By "isotropic phase" or "isotropic" is meant a liquid crystal phase where the liquid crystals have no significant positional order or directional order. By "nematic phase" or "nematic" is meant a liquid crystal phase where the liquid crystals have no significant positional order, but have a detectable directional order. In some instances, the liquid crystal phase transition occurs in response to a stimulus applied to the liquid crystals. The stimulus may be any convenient stimulus that can induce a phase transition in the liquid crystals, such as, but not limited to, a change in temperature, an electrical stimulus, a magnetic stimulus, combinations thereof, and the like. In some cases, the stimulus that induces the phase transition in the liquid crystal is a change in temperature, e.g., heating or cooling. As such, the liquid crystalline fluid may be composed of a liquid crystal that has a temperature dependent phase transition. In some embodiments, the liquid crystalline fluid undergoes a phase transition from an isotropic phase to a nematic phase when the temperature of the liquid crystalline fluid is reduced to below the phase transition temperature. In some embodiments, the liquid crystalline fluid undergoes a phase transition from a nematic phase to an isotropic phase when the temperature of the liquid crystalline fluid is increased to above the phase transition temperature.

In certain embodiments, a temperature dependent liquid crystalline fluid has a phase transition temperature that is lower than the phase transition temperature of an organic ligand (or an organic ligand-functionalized nanoparticle) as described herein. As such, in some instances, the phase transition temperature (e.g., melting temperature or clearing point) of the organic ligand (or organic ligand-functionalized nanoparticle) is greater than the phase transition temperature of the liquid crystalline fluid. In certain instances, a temperature dependent liquid crystalline fluid has a phase transition temperature (e.g., for a phase transition between an isotropic phase and a nematic phase) ranging from 20° C. to 50° C., such as 25° C. to 45° C., or 30° C. to 40° C. In some cases, a temperature dependent liquid crystalline fluid has a phase transition temperature (e.g., for a phase transition between an isotropic phase and a nematic phase) of approximately 35° C., such as 34° C. Examples of liquid crystalline fluids that have a temperature dependent phase transition include, but are not limited to, 4-cyano-4'-pentylbiphenyl (5CB), and the like.

The nanoparticles may be dispersed in the mesomorphic material, such as liquid crystalline fluid, using any convenient method, such as, but not limited to, mixing, vortexing, shaking, applying sound energy (also referred to as "sonication" herein), combinations thereof, and the like. In some cases, the method includes applying sound energy to the nanoparticles in mesomorphic material to disperse the nanoparticles in the mesomorphic material. The nanoparticles may be dispersed in the mesomorphic material such that the nanoparticles are substantially evenly distributed throughout the mesomorphic material. For example, a mixture of the nanoparticles and mesomorphic material may be substantially homogeneous. In certain embodiments, the nanoparticles are dispersed in the mesomorphic material at room temperature (e.g., ~25° C.). In other cases, the nanoparticles are dispersed in the mesomorphic material at a temperature other than room temperature, e.g., lower or higher than room temperature. In some instances, the nanoparticles are dispersed in the mesomorphic material at a temperature higher than room temperature. In certain embodiments, the nanoparticles are dispersed in the mesomorphic material at a temperature where the nanoparticles are present in a desired phase of the mesomorphic material, such as an isotropic phase or a nematic phase. For instance, embodiments of the methods include dispersing the nanoparticles in the mesomorphic material at a temperature where the nanoparticles are present in an isotropic phase of the mesomorphic material. In certain aspects, the temperature where the nanoparticles are present in an isotropic phase of the mesomorphic material is a temperature above the phase transition temperature of the mesomorphic material, such as a temperature ranging from 20° C. to 50° C., such as 25° C. to 45° C., or 30° C. to 40° C., such as a temperature of approximately 35° C., for example 34° C.

Embodiments of the method of producing the self-assembled microcapsules described herein also include inducing a phase transition in the mesomorphic material (e.g., the liquid crystalline liquid) to produce the self-assembled microcapsules. In certain embodiments, the phase transition of the mesomorphic material is a phase transition from an isotropic phase to a nematic phase. Thus, the method may include inducing a phase transition from an isotropic phase to a nematic phase in the mesomorphic material.

In some instances, inducing a phase transition in the mesomorphic material (e.g. a liquid crystalline liquid) is performed by applying a stimulus to the mesomorphic material. The stimulus may be any convenient stimulus that can induce a phase transition in the mesomorphic material, such as, but not limited to, a change in temperature, an electrical stimulus, a magnetic stimulus, combinations thereof, and the like. In some cases, inducing the phase transition in the mesomorphic material is accomplished by changing the temperature of the mesomorphic material, e.g., heating or cooling the mesomorphic material. In certain instances, inducing the phase transition in the mesomorphic material is accomplished by decreasing the temperature of the mesomorphic material to a temperature below the phase transition temperature of the mesomorphic material. Reducing the temperature of the mesomorphic material to a temperature below the phase transition temperature of the mesomorphic material may induce a phase transition of the mesomorphic material from an isotropic phase to a nematic phase. In some cases, at the isotropic to nematic phase transition in a homogeneous mesomorphic material, domains of nematic ordering form and grow as the mesomorphic material is cooled through the transition temperature. As the nematic domains form and increase in size, isotropic domains began decreasing in size. In some instances, the dispersed nanoparticles (e.g., organic ligand-functionalized nanoparticles) in the mesomorphic material may preferentially locate in the shrinking isotropic domains. As the nanoparticles aggregate at the interface between the isotropic and nematic domains or mesomorphic state, the nanoparticles may form a microcapsule of stably associated nanoparticles as described herein. For example, a microcapsule may be produced, such as a shell configuration having a spherical surface. Without being bound to any particular theory, by controlling the phase transition process rate can control the size of the microcapsule being formed. In certain instances, slowing the cooling rate of the mesomorphic material (e.g. a liquid crystalline liquid) results in larger microcapsules being formed.

Methods

Aspects of the present disclosure include methods of delivering one or more substrates to an individual, where the substrate is released from a self-assembled microcapsule described herein by activation with one or more external stimulus, wherein the organic ligands undergo electron transfer upon activation with the external stimulus to rupture the microcapsule, thereby releasing the one or more encapsulated substrates. The method of delivering one or more substrates to an individual includes administering an effective amount of a self-assembled microcapsule composed of nanoparticles, stimuli-responsive organic ligands attached to the nanoparticles and one or more substrates encapsulated inside the microcapsule; and applying one or more external stimulus to rupture the microcapsule and release the one or more substrates. The self-assembled microcapsule used in the method may be composed of any organic ligand functionalized nanoparticles as described herein. For instance, the nanoparticles may be functionalized with an organic ligand of the formulae (I), (IA), (II) or (IIA), or a structure of any of organic ligands (1) to (8) as described herein.

In certain embodiments of the methods of delivering one or more substrates to an individual, the self-assembled microcapsule may be composed of nanoparticles substituted with an organic ligand selected from (1)-(8) as described herein. In some embodiments of the methods described herein, the nanoparticles are substituted with an organic ligand according to formula (I) or (II) as described herein. In some embodiments of the methods of delivering one or more substrates to an individual, the self-assembled microcapsule may be composed of gold nanoparticles substituted with an organic ligand as described herein. In some embodiments of the methods of delivering one or more substrates to an individual, the self-assembled microcapsule may be composed of non-metallic nanoparticles substituted with an organic ligand as described herein. In certain embodiments of the methods, the nanoparticles are densely packed so as to prevent leakage of the encapsulated substrate over a period of several months and allow rapid release of the substrate when activated with an external stimulus. In some cases, the mean inter-particle separation of the nanoparticles in the microcapsule wall is about 10 nm to 20 nm.

In certain embodiments of the method, the self-assembled microcapsules are stable upon application of heat up to a temperature of 240° C., such as from 100 to 240° C., 120 to 240° C., 140 to 240° C., 160 to 240° C., 180 to 240° C., 200 to 240° C. or 220 to 240° C.

Aspects of the methods include activation from an external stimulus, wherein upon activation the organic ligands undergo electron transfer to release the one or more substrates encapsulated within the self-assembled microcapsules as described herein. It will be understood that any convenient external stimulus which activates the organic ligands to affect microcapsule rupture may be used. In some embodiments, activation is achieved with an electrical input. In certain cases, the electrical input is adjusted based on defined electronic properties of the organic ligand. In some cases, the electrical input is applied at a voltage of 300 mV or more, such as 400 mV or more, 500 mV or more, 600 mV or more, 700 mV or more, 800 mV or more, 900 mV or more or 1000 mV or more, or even more. In some cases, the electrical input is applied at a voltage of 1 V or more, such as 2 V or more, 3 V or more, 4 V or more, 5 V or more, 6 V or more, 7 V or more, 8 V or more, 9 V or more, 10 V or more, 20 V or more, 30 V or more, 40 V or more, 50 V or more, 60 V or more, 70 V or more, 80 V or more, 90 V or more or 100 V or more, or even more. In some cases, the electrical input is applied at a voltage of 100 V or more, such as 200 V or more, 300 V or more, 400 V or more, 500 V or more, 600 V or more, 700 V or more, 800 V or more, 900 V or more or 1000 V or more, or even more. In some cases, the electrical input is applied at a voltage of 1 kV or more, such as 2 kV or more or 3 kV or more, or even more. In certain instances, the electrical input is applied at a voltage from 300 mV to 3 kV, such as 300 mV to 2 kV, 300 mV to 1 kV, 300 mV to 0.5 kV, 300 mV to 0.1 kV, 300 mV to 0.05 kV, 300 mV to 0.01 kV.

In certain instances, the electrical input is less than 3 kV, such as 2 kV or less or 1 kV or less, or even less. In some cases, the electrical input is less than 1000 V, such as 900 V or less, 800 V or less, 700 V or less, 600 V or less, 500 V or less, 400 V or less, 300 V or less, 200 V or less, 100 V or less, 90 V or less, 80 V or less, 70 V or less, 60 V or less, 50 V or less, 40 V or less, 30 V or less, 20 V or less, 10 V or less, or even less. In some cases, the electrical input is less than 10 V, such as 9 V or less, 8 V or less, 7 V or less, 6 V or less, 5 V or less, 4 V or less, 3 V or less, 2 V or less, 1 V or less, or even less. In some cases, the electrical input is less than 1000 mV, such as 900 mV or less, 800 mV or less, 700 mV or less, 600 mV or less, 500 mV or less, 400 mV or less, 300 mV or less, or even less. In certain instances, the electrical input is applied at a voltage from 300 mV to 1500 mV, such as 300 mV to 1200 mV, 300 mV to 1000 mV, 300 mV to 800 mV, 300 mV to 600 mV, 300 mV to 500 mV or 300 mV to 400 mV.

In some embodiments of the method, the external stimulus is an electrical input and the electrical input is applied for a duration of 60 minutes or less to rupture the microcapsule, such as 50 minutes or less, 40 minutes or less, 30 minutes or less, 20 minutes or less, 10 minutes or less or even less. In certain instances, the electrical input is applied for a duration of 10 minutes or less to rupture the microcapsule, such as 9 minutes or less, 8 minutes or less, 7 minutes or less, 6 minutes or less, 5 minutes or less, or even less. In certain cases, the electrical input is applied for a duration of about 10 minutes to rupture the microcapsule. In certain cases, the electrical input is applied for a duration of 5 minutes or less to rupture the microcapsule.

Electrical input delivering devices that may be employed in the practice of the subject methods typically include a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of a representative electrode suitable for use in the subject methods is applicable to other electrodes that may be employed.

The electrode employed in the subject method is typically controllable to provide output signals that may be varied in voltage, frequency, pulse width, current and intensity. The electrode is typically one that provides both positive and negative current flow from the electrode and/or is capable of stopping current flow from the electrode and/or changing the direction of current flow from the electrode. For example, embodiments include an electrode that is controllable in these respects, i.e., controllable in regard to producing positive and negative current flow from the electrode, stop current flow from the electrode, change direction of current flow from the electrode, and the like. In certain embodiments, the electrode has the capacity for variable output, linear output and short pulse width.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed.

A controller or programmer is also typically included in an electrical input device. The programmer is typically one or more microprocessors under the control of a suitable software program. Other components of the programmer will be apparent to those of skill in the art, e.g., analog to digital converter, etc.

The electric input device employed in the practice of the subject methods may be pre-programmed for desired parameters. In many embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician.

In some embodiments of the method, the stimuli-responsive organic ligands are sound-responsive and upon activation with sound energy the microcapsule ruptures to release the encapsulated substrate. In some cases, the sound energy is applied at a frequency of 20 kHz or more, such as 25 kHz or more, 30 kHz or more, 35 kHz or more, 40 kHz or more, or even more. In some cases, the sound energy is applied at a frequency of 40 kHz or less, such as 35 kHz or less, 30 kHz or less, 25 kHz or less, 20 kHz or less, or even less. In some cases, the sound energy is applied at a frequency from 20 kHz to 40 kHz, such as 20 kHz to 25 kHz, 25 kHz to 35 kHz, 35 kHz to 40 kHz.

The sound energy can also be characterized by a waveform that is defined by amplitude (i.e., loudness), or any other sinusoidal properties. Where the sound stimulus is represented as a waveform, loudness is also referred to herein as amplitude. Loudness can range from about 1 to about 5 dB, about 5 to about 10 dB, about 10 to about 40 dB, about 40 to about 60 dB, about 60 to about 70 dB, or about 80 dB or more. For an individual with healthy hearing capability, loudness of the noise should be no more than about 85 dB, no more than about 80 dB, no more than about 75 dB or less. For example, in the subject methods, the sound energy can be delivered at a level of about 65 dB or less, 55 dB or less, 45 dB or less, 35 dB or less, 25 dB or less, 15 dB or less, 5 dB or less, or even less.

In some embodiments of the method, the external stimulus is sound energy and the sound energy is applied for a duration of 60 minutes or less to rupture the microcapsule, such as 50 minutes or less, 40 minutes or less, 30 minutes or less, 20 minutes or less, 10 minutes or less or even less. In certain instances, the sound energy is applied for a duration of 10 minutes or less to rupture the microcapsule, such as 9 minutes or less, 8 minutes or less, 7 minutes or less, 6 minutes or less, 5 minutes or less, or even less. In certain cases, the sound energy is applied for a duration of about 10 minutes to rupture the microcapsule. In certain cases, the sound energy is applied for a duration of 5 minutes or less to rupture the microcapsule.

In certain embodiments of the method, full release of the substrate is obtained within 5 minutes or less from the time of application of the external stimulus, such as 4 minutes or less, 3 minutes or less, 2 minutes or less, 1 minute or less, or even less.

In certain embodiments of the method, a mixture of self-assembled microcapsules, each comprising different stimuli-responsive organic ligands is administered. In certain cases, the external stimulus is adjusted to selectively target a specific self-assembled microcapsule comprising an associated stimuli-responsive organic ligand within the mixture of self-assembled microcapsules.

In some instances of the methods disclosed herein, during activation of the self-assembled microcapsules with an external stimulus (e.g., an electrical input or sound energy) electron transfer is observed, causing release of the substrates encapsulated within. Without being bound to any particular theory, it is believed that the microcapsules rupture due to a weakening of the shell wall caused by a conformational change of the organic ligands attached to the nanoparticles after electron transfer.

Utility

The self-assembled microcapsules of the present disclosure find use in applications such as the encapsulation of active agents and live cells and release of the encapsulated substrates upon activation with an external stimulus (e.g., an electrical input or sound energy). Encapsulation of the active agent inside the microcapsule may facilitate one or more of: delivery of the active agent to a desired site; formulation of the active agent into a desired formulation; increased stability of the active agent; controlled release of the active agent; delayed release of the active agent; and the like. The self-assembled microcapsules of the present disclosure find particular use in targeted controlled release of its encapsulated cargo to a living host, such that at the site of release in the living host the surrounding healthy tissue is not damaged. The self-assembled microcapsules of the present disclosure also find use in targeted controlled release of its encapsulated cargo at any targeted location, such as at a site of release in a living host, or an environment that does not include a living host, such as a chemical solution.

Kits

Aspects of the present disclosure additionally include kits that include self-assembled microcapsules as described in detail herein. In some instances, the kit includes one or more containers for containing the self-assembled microcapsules with one or more substrates encapsulated inside the microcapsule. In certain embodiments, the container may be a sealed packaging, e.g., in a water vapor-resistant container, optionally under an air-tight and/or vacuum seal. In certain instances, the packaging is a sterile packaging, configured to maintain the microcapsules enclosed in the packaging in a sterile environment. By "sterile" is meant that there are substantially no microbes (such as fungi, bacteria, viruses, spore forms, etc.). The kits may further include a fluid (e.g., a liquid). For instance, the kit may include a liquid, such as a liquid in which the microcapsule structures are provided. For example, the microcapsule may be dispersed in the liquid. Liquids in which the microcapsules may be dispersed include, but are not limited to, a mesomorphic material (e.g., liquid crystalline liquid), a solvent (e.g., a pharmaceutically acceptable organic solvent), and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1—Organic Ligand Synthesis

Scheme 1: General Procedure for Synthesis of Bis(Imino) Pyridine Organic Ligands of Formula (I), (II) and (IIA)

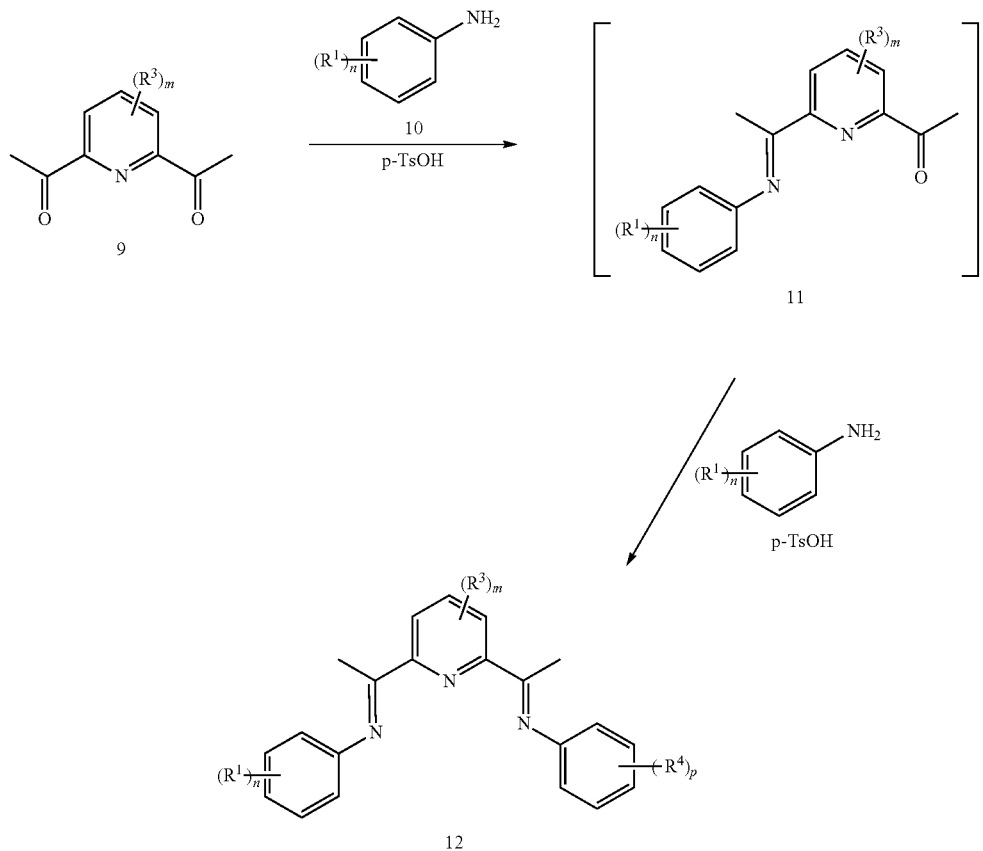

With reference to Scheme 1, $R^3$, $R^1$, $R^4$, n, m and p are as defined herein. In some cases, compounds 9 and 10 are commercially available.

Synthesis of Exemplary Organic Ligand

In some embodiments, the subject organic ligands were synthesized according to Scheme 1. Preparation of bis (imino)pyridine ligand core 12 was achieved via coupling between 2,6 diacetylpyridine 9 and aniline derivative 10 to afford imino pyridine intermediate 11. A second coupling between compound 11 and a second aniline derivative affords bis(imino)pyridine ligand core 12.

Exemplary Organic ligand: Bis(Imino)Pyridine, Compound (6)

Dry toluene (30 mL) was added to a 100 mL flame dried round bottom flask, followed by 2,6 diacetylpyridine (0.442 g, 2.71 mmol) and freshly distilled 2,6 dimethylaniline (0.690 g, 2.1 mmol). Then p-toluenesulfonic acid (p-TsOH) was added (0.077 g, 15 mol %). The reaction mixture was refluxed with a Dean-Stark apparatus for 24 hours. The solution was then cooled to room temperature and quenched with saturated sodium bicarbonate. The resulting solution was transferred to a separatory funnel and extracted with DCM (3×50 mL). The solvent was evaporated, and the residue was crystalized in absolute ethanol (15 mL) overnight to yield compound 6 (600 mg, 60% yield).

Scheme 2: General procedure for synthesis of mono(imino)pyridine organic ligands of formula (I) and (IA)

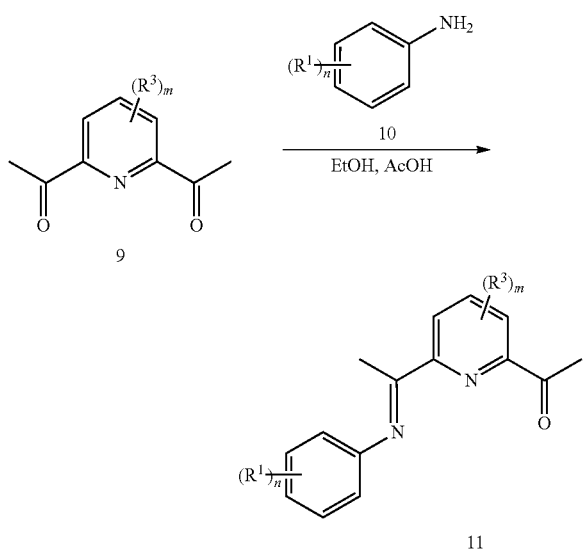

In other embodiments, the subject organic ligands were synthesized according to Scheme 2. Preparation of mono (imino)pyridine ligand core 11 was achieved via coupling between 2,6 diacetylpyridine 9 and aniline derivative 10 in the presence of trace glacial acetic acid.

Exemplary Organic ligand: Mono Imino Pyridine, Compound (1)

A flamed dried 50 mL round bottom flask was charged with absolute ethanol (25 mL) followed by 2,6 diacetyl pyridine (0.442 g, 2.71 mmol) and 0.690 mLs of 2,6 dimethylaniline (0.690 mL, 2.1 mmol). Five drops of glacial acetic acid were added, and the solution was refluxed for 18 hours, then allowed to cool to room temperature. The reaction was quenched with saturated sodium bicarbonate (25 mL) and extracted with DCM. The DCM was evaporated and kept at −20° C. overnight. The resulting yellow needles were washed with cold ethanol and dried under reduced pressure to afford compound (1).

Example 2—Microcapsule Formation

The subject nanocapsules were prepared according to the procedures outlined in Quint et al. (2017) Scientific Reports 7(1):17788, the disclosure of which is incorporated by reference herein.

The organic ligands used in this example were Compounds (5)-(8). The ligand molecules contained a bis(imino)pyridine core region surrounded by various substituents on the aromatic rings which modified the electronics and sterics of the binding. The nitrogen atoms of the organic ligands bound to the nanoparticle surface in the ligand exchange process. Ligands were attached (also referred to herein as "exchanged") on to the surface of commercial gold nanoparticles (AuNPs).

Microcapsule size was controlled by the properties and functionality of the organic ligand. By varying the ligand composition and functionality, comprehensive control over the shell diameters may be achieved. For example, FIG. 6, panels A is a scanning electron microscopy (SEM) image of a microcapsule (made with compound (5)) with a diameter of 200 nm. The subject microcapsule diameters can be tuned controllably between 200 nm-2 μm by varying the functionalization of the nanoparticles.

Figure 2:
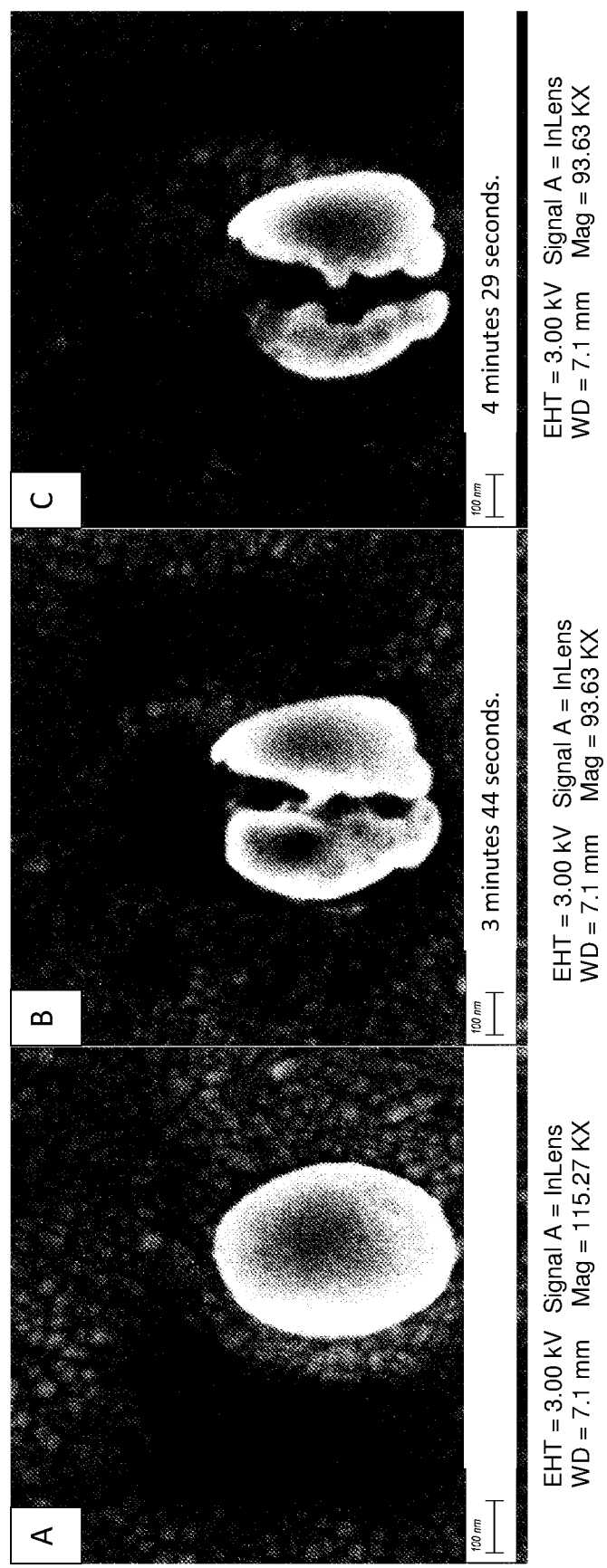
FIG. 2, panels A-C, show scanning electron microscope (SEM) images of the rupture of an exemplary self-assembled microcapsule composed of Cd/Sn/Se nanoparticles and compound (7) upon activation with an electrical stimulus. Panel A, shows a scanning electron microscope image of an intact self-assembled microcapsules composed of Cd/Sn/Se nanoparticles and exemplary compound (7). Panel B, shows a scanning electron microscope image of the ruptured self-assembled microcapsules composed of Cd/Sn/Se nanoparticles and exemplary compound (7) after 3 minutes 44 seconds. Panel B, shows a scanning electron microscope image of the ruptured self-assembled microcapsules composed of Cd/Sn/Se nanoparticles and exemplary compound (7) after 4 minutes 29 seconds.
Figure 3:
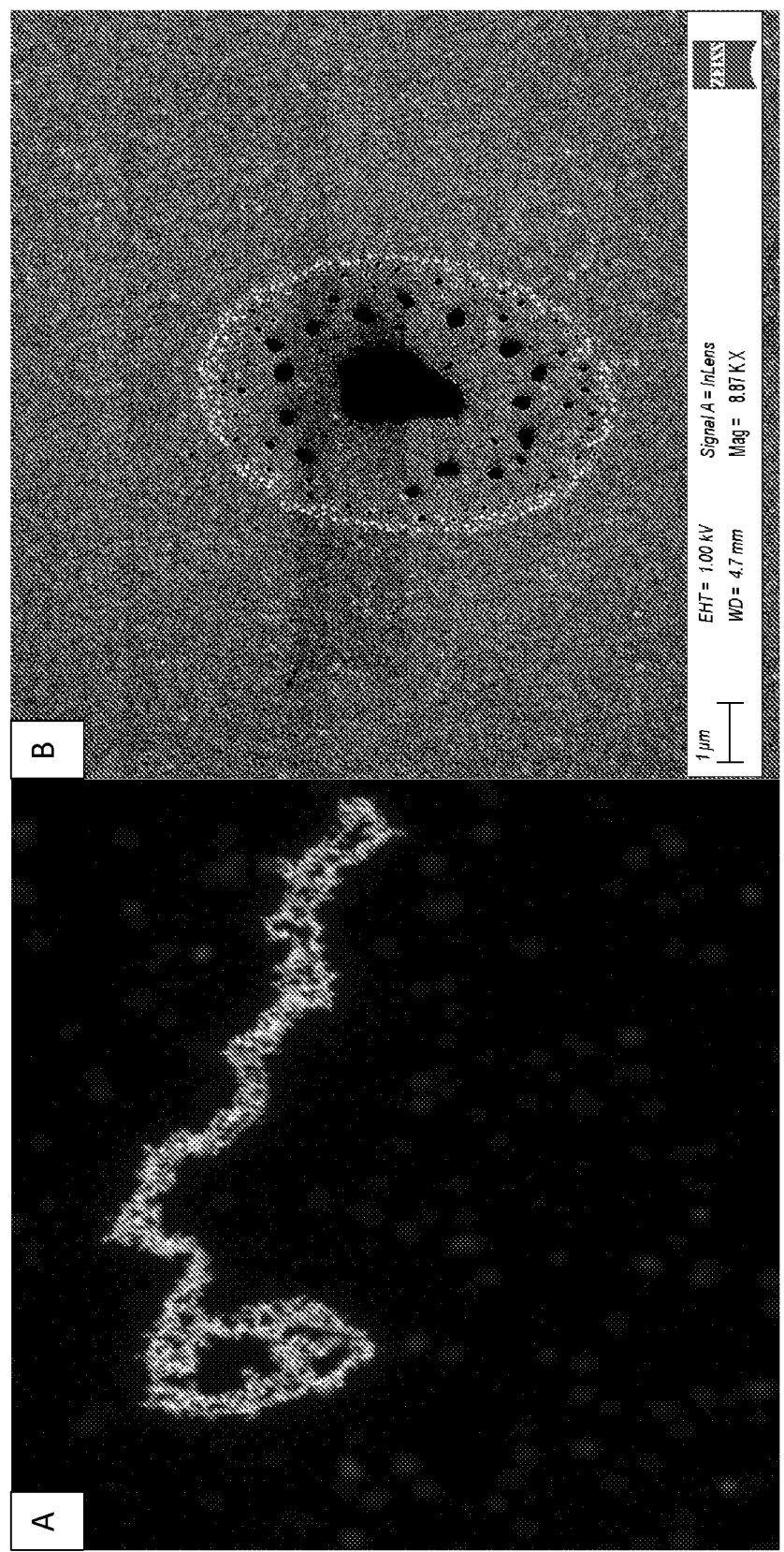
FIG. 3, panels A-B, show scanning electron microscope (SEM) images of self-assembled microcapsules composed of Cd/Sn/Se nanoparticles and exemplary compound (8).
Figure 4:
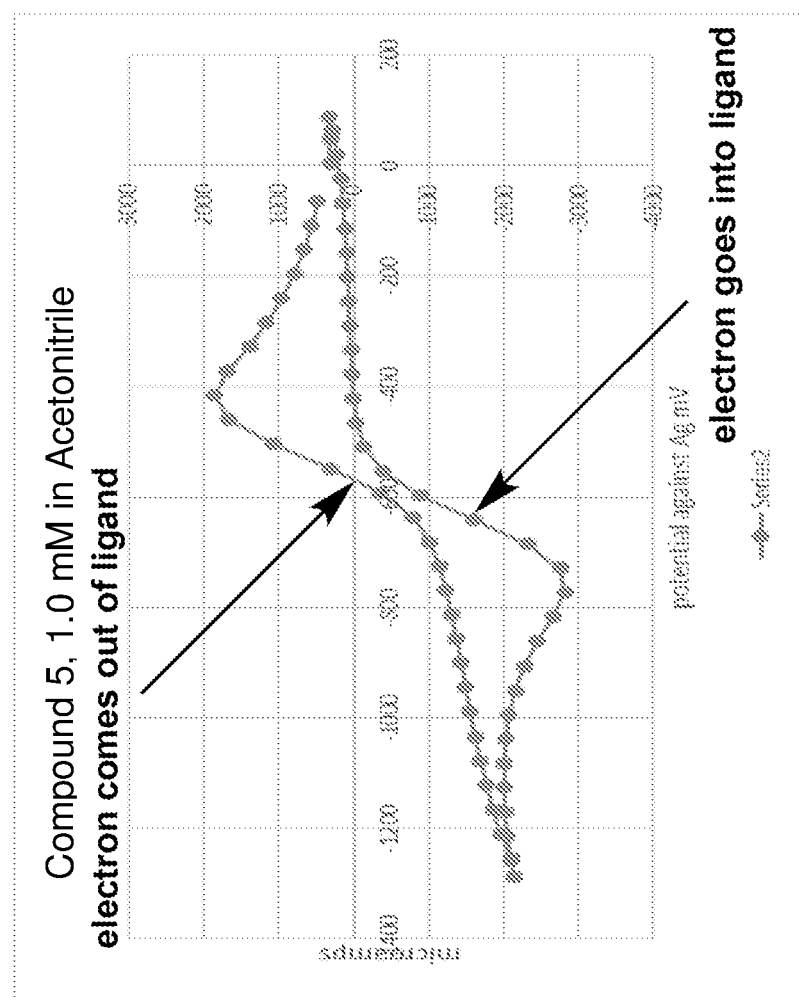
FIG. 4, depicts graphically the electron transfer of exemplary organic ligand (5). Segment=6, Direction=falling, initial V=0, upper V=0, Lower V=−1.3, Final V=0, Sweep rate (mV/s)=80, peak anodic/peak cathodic=0.66.

Structural Characterization Using scanning electron microscopy, (SEM), microcapsule formation was observed, e.g., see FIG. 2 (Compound 7), FIG. 3 A (Compound 7), FIG. 4 (Compound 8) and FIG. 6 A (Compound 5).

Example 3—Microcapsule Breaking Procedure

The electronic properties of the ligand molecules allow for leverage of stimulus such as electrical input or sound energy to disrupt the shell wall. Activation with an electrical stimulus adds considerable versatility to the possible applications that the subject self-assembled microcapsules may be suited for. For example, electrical impulses are known to penetrate solid materials, such as living/human tissue, thus offering a new selective and mild method of payload delivery to a targeting site in an individual. In addition, the subject microcapsules may be composed of non-metallic nanoparticles, since plasmonic resonance is not necessary for shell disruption and payload release. Avoiding light would also prevent the negative side-effects of photothermal heating when optical excitation is used.

FIG. 2, panels A to C, shows a series of SEM images of an intact self-assembled microcapsule made with organic ligand, compound (7) (panel A), and the microcapsule rupturing upon activation with an electrical input (panels B and C). Panel B shows the extent of the microcapsule rupture after 3 minutes and 44 seconds. Panel C shows the extent of the microcapsule rupture after 4 minutes and 29 seconds.

Figure 5:
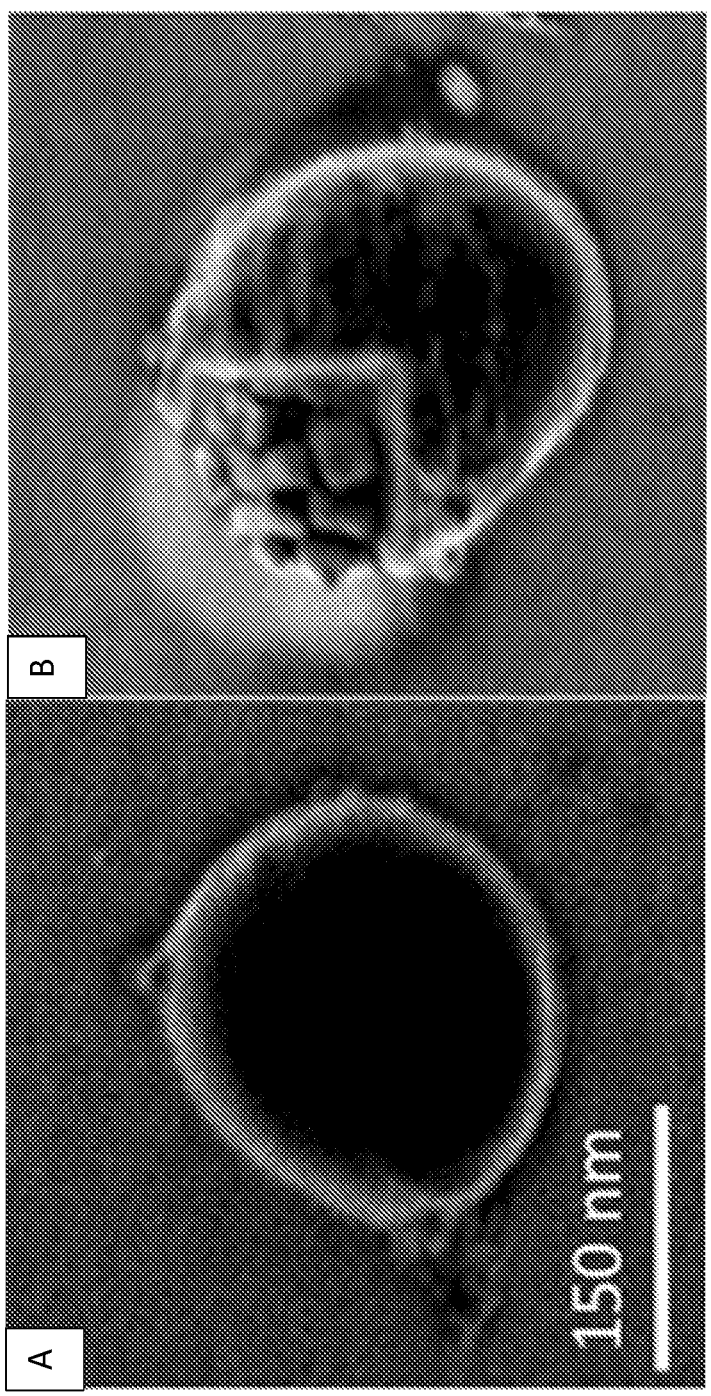
FIG. 5, panels A-D, shows scanning electron microscope (SEM) images of a 200 nm exemplary self-assembled microcapsules composed of 6 nm Cd/Sn/Se quantum dots and compound (5). Panel A, a scanning electron microscope image of an intact self-assembled microcapsules composed of 6 nm Cd/Sn/Se quantum dots and compound (5). Panel B-D, show the self-assembled microcapsules composed of 6 nm Cd/Sn/Se quantum dots and compound (5) progressively rupturing under applied voltage.

FIG. 5, panels B-D, shows a series of SEM images of an intact self-assembled microcapsule made with exemplary organic ligand, compound (5) (panel A), and the microcapsule progressively rupturing upon activation with an electrical input (panels B to D).

FIG. 4 depicts graphically electron transfer via exemplary organic ligand, Compound (5). This graph shows that electron transfer into compound (5) is reversible.

The voltage required to add an electron into the organic ligand varies with the structure of the organic ligand. Without being bound to any particular theory, it is believed that by varying the nature of the organic ligands in the self-assembled microcapsule, certain organic ligands may become 'activated' and lead to microcapsule rupture in the presence of self-assembled microcapsules bearing different organic ligands. As such, the organic ligand structure may be altered to affect both microcapsule formation (e.g., changes in size and shape of the 3-D nanomaterials) and the electrical current required to disrupt their binding interactions to lead to microcapsule rupture. Self-assembled microcapsules of similar characteristics may be made with different ligands, such that an electrical impulse can selectively target only specific self-assembled microcapsules based on the electronic capabilities of the associated organic ligand.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A self-assembled microcapsule comprising:
nanoparticles; and
electro-responsive organic ligands attached to said nanoparticles;
wherein the organic ligands undergo electron transfer upon activation with an electrical input to produce a nanomaterial with openings, and
wherein the organic ligand is of formula (I):

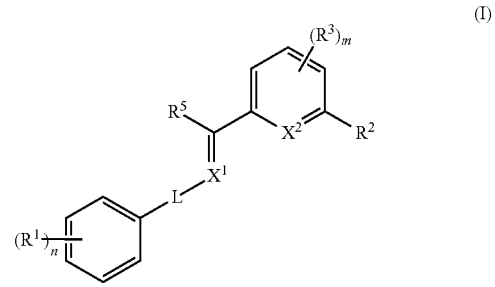

wherein:
$X^1$ and $X^2$ are each independently selected from N and $CR^7$, wherein each $R^7$ is independently selected from H, halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
L is a bond or a linker;
$R^1$ and $R^3$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;
$R^2$ is selected from H, halogen, hydroxyl, azido, acyl, substituted acyl, imine, substituted imine, alkyl, substituted alkyl, alkenyl, substituted alkenyl, alkynyl, substituted alkynyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof $R^5$ is selected from H, alkyl, substituted alkyl, aryl, and substituted aryl;

n is an integer from 0 to 5; and m is an integer from 0 to 3.

2. The self-assembled microcapsule of claim 1, wherein each organic ligand is attached to said nanoparticles through more than one binding site.

3. The self-assembled microcapsule of claim 1, wherein the amount of electrical input is adjusted based on defined electronic properties of the organic ligand.

4. The self-assembled microcapsule of claim 1, wherein the electrical input is applied at a voltage of from 300 mV to 3 kV.

5. The self-assembled microcapsule of claim 4, wherein the electrical input is applied at a voltage of from 300 mV to 1500 mV.

6. The self-assembled microcapsule of claim 1, wherein the electrical input is applied for a duration of one hour or less to produce the nanomaterial with openings.

7. The self-assembled microcapsule of claim 1, wherein the organic ligand is of the formula (IA):

(IA)

wherein:

L is a bond, or a linker;

$R^1$ and $R^3$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

$R_5$ and $R_8$ are each independently selected from H, alkyl, substituted alkyl, aryl, and substituted aryl;

n is an integer from 0 to 5; and m is an integer from 0 to 3.

8. The self-assembled microcapsule of claim 1, wherein the organic ligand is of formula (II):

(II)

wherein $X^1$, $X^2$ and $X^3$ are each independently selected from N and $CR^7$, wherein each $R^7$ is independently selected from H, halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

L is a bond, or a linker;

$R^1$, $R^3$ and $R^4$ are each independently selected from halogen, hydroxyl, azido, alkyl, substituted alkyl, alkenyl, substituted alkenyl, alkynyl, substituted alkynyl, acyl, substituted acyl, $C_1$-$C_{12}$ alkoxy, substituted $C_1$-$C_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

$R^5$ and $R^6$ are each independently selected from H, alkyl, substituted alkyl, aryl, and substituted aryl;

n is an integer from 0 to 5;

m is an integer from 0 to 3; and p is an integer from 0 to 5.

9. The self-assembled microcapsule of claim 8, wherein the organic ligand is of the formula (IIA):

(IIA)

wherein:

L is a bond or a linker;

R$^1$, R$^3$ and R$^4$ are each independently selected from halogen, hydroxyl, azido, alkyl, substituted alkyl, alkenyl, substituted alkenyl, alkynyl, substituted alkynyl, acyl, substituted acyl, C$_1$-C$_{12}$ alkoxy, substituted C$_1$-C$_{12}$ alkoxy, amino, substituted amino, cycloalkyl, substituted cycloalkyl, heterocycloalkyl, substituted heterocycloalkyl, aryl, substituted aryl, heteroaryl, substituted heteroaryl, phosphate, substituted phosphate, phosphoryl, substituted phosphoryl, thiol, and substituted thiol, and combinations thereof;

R$^5$ and R$^6$ are each independently selected from H, alkyl, substituted alkyl, aryl, and substituted aryl;

n is an integer from 0 to 5;

m is an integer from 0 to 3; and p is an integer from 0 to 5.

10. The self-assembled microcapsule of claim 1, wherein the organic ligand is selected from the group consisting of:

(1)

(2)

(3)

(4)

(5)

(6)

(7) and (8)

and combinations thereof.

11. The self-assembled microcapsule of claim 1, wherein the mean inter-particle separation of the nanoparticles is from 1 nm to 100 nm.

12. The self-assembled microcapsule of claim 1, wherein the nanoparticles are composed of a material selected from a semiconductor material, a metal, a metal oxide, a metalloid, a metal coated material, an oxide, a magnetic material, a nanosome, a lipidsome and a polymer, and combinations thereof.

13. The self-assembled microcapsule of claim 1, wherein one or more substrates is encapsulated inside the microcapsule.

14. The self-assembled microcapsule of claim 13, wherein at least one substrate is an active agent.

15. The self-assembled microcapsule of claim 13, wherein the substrate is released upon activation with the external stimulus.

16. A composition comprising:

a liquid; and a self-assembled microcapsule of claim 1 in the liquid.

17. A method of delivering one or more substrates to an individual, the method comprising:
- administering an effective amount of a self-assembled microcapsule of claim 1; and one or more substrates encapsulated inside the microcapsule, to an individual; and
- applying one or more external stimulus, wherein the organic ligands undergo electron transfer upon activation with the external stimulus to rupture the microcapsule and release the one or more substrates.

18. A kit for delivering one or more substrates to an individual, the kit comprising:
- one or more containers comprising a self-assembled microcapsule of claim 1; and
- one or more substrates encapsulated inside the microcapsule.

* * * * *